(12) United States Patent
Mason et al.

(10) Patent No.: US 10,603,479 B2
(45) Date of Patent: Mar. 31, 2020

(54) VASCULAR ACCESS DEVICE AND METHOD

(71) Applicant: Access for Life Inc., Fleetwood, NY (US)

(72) Inventors: Roger Mason, Blytheville, AR (US); Philip Libman, Shaarei Tikva (IL); Yehuda Zicherman, Shoham (IL); Noam Hadas, Tel-Aviv (IL); David Grey, Ramat-Gan (IL)

(73) Assignee: Access for Life Inc., Fleetwood, NY (US)

( * ) Notice: Subject to any disclaimer, the term of this patent is extended or adjusted under 35 U.S.C. 154(b) by 0 days.

(21) Appl. No.: 16/114,290

(22) Filed: Aug. 28, 2018

(65) Prior Publication Data

US 2020/0069929 A1  Mar. 5, 2020

(51) Int. Cl.
*A61M 39/02* (2006.01)
*A61M 1/36* (2006.01)
*A61M 1/30* (2006.01)

(52) U.S. Cl.
CPC .......... *A61M 39/0208* (2013.01); *A61M 1/30* (2013.01); *A61M 1/3655* (2013.01); *A61M 1/3656* (2014.02); *A61M 1/3661* (2014.02); *A61M 2039/0238* (2013.01); *A61M 2039/0244* (2013.01); *A61M 2205/18* (2013.01); *A61M 2205/3306* (2013.01);
(Continued)

(58) Field of Classification Search
CPC .. A61M 2039/0244; A61M 2039/0202; A61M 2039/0205; A61M 2039/0238; A61M 2039/0258; A61M 2039/0267; A61M 2039/0276; A61M 39/0247; A61M 39/02; A61M 39/0208; A61M 1/3656; A61M 1/30; A61M 1/3653; A61M 1/3655; A61M 1/3659; A61M 1/3661
See application file for complete search history.

(56) References Cited

U.S. PATENT DOCUMENTS 6,913,609 B2  7/2005  Yencho et al.
8,414,530 B2  4/2013  Mason
(Continued)

FOREIGN PATENT DOCUMENTS

EP  2859911 A1 *  4/2015  ........... A61B 5/6865
WO  WO 2010/088532  8/2010
(Continued)

*Primary Examiner* — Kami A Bosworth
*Assistant Examiner* — Leah J Swanson

(57) ABSTRACT

A vascular access device is disclosed including a needle insertion guide having a proximal end and a distal end a the guide including a needle insertion guide having a proximal end and a distal end and a vessel interface configured for attaching the distal end of the guide to a target on an unbroken outer wall of a blood vessel of a living subject and a skin interface configured for attaching the proximal end of the guide to a skin of the living subject. Optionally the vessel interface is connected to the guide by a flexible joint configured. Optionally two vascular access devices are connected by an electrically conductive connection. Optionally the vascular access device includes a sensor to determine when a needle enters the blood vessel. Optionally the vascular access device serves as a marker for a sensor determining a status of the blood vessel.

34 Claims, 29 Drawing Sheets

(52) U.S. Cl.
CPC ............... *A61M 2205/3317* (2013.01); *A61M 2205/3375* (2013.01); *A61M 2205/52* (2013.01); *A61M 2205/8206* (2013.01)

(56) References Cited

U.S. PATENT DOCUMENTS

| | | | |
|---|---|---|---|
| 2007/0078391 A1* | 4/2007 | Wortley | A61M 39/0208 604/116 |
| 2008/0195021 A1* | 8/2008 | Roger | A61M 1/3653 604/4.01 |
| 2009/0131767 A1* | 5/2009 | Arne | A61B 5/6862 600/302 |
| 2009/0326611 A1* | 12/2009 | Gillbe | A61N 1/3787 607/61 |
| 2013/0116665 A1* | 5/2013 | Humayun | A61M 5/162 604/891.1 |
| 2013/0245550 A1 | 9/2013 | Young et al. | |
| 2014/0276573 A1* | 9/2014 | Miesel | A61M 5/329 604/506 |
| 2016/0198961 A1* | 7/2016 | Homyk | A61B 5/0082 600/476 |

FOREIGN PATENT DOCUMENTS

| | | | | |
|---|---|---|---|---|
| WO | WO-2016111650 A1 | * | 7/2016 | ......... A61M 1/3653 |
| WO | WO-2016183145 A1 | * | 11/2016 | ........ A61M 39/0208 |

* cited by examiner

VASCULAR ACCESS DEVICE AND METHOD

FIELD AND BACKGROUND OF THE INVENTION

The present invention, in some embodiments thereof, relates to a vascular access system and, more particularly, but not exclusively, to a system for facilitating access to a blood vessel and monitoring the access.

PCT/US2016/031771 published under WO 2016/183145 describes a Vascular Access Device (VAD) that may be used for example in hemodialysis.

SUMMARY OF THE INVENTION

According to an aspect of some embodiments of the invention, there is provided an implantable device for vascular access including: a guide including a lumen of shaped and sized to fit a hemodialysis needle constraining the needle to an angle of less than 5 degrees with respect to the lumen and constraining a position of a distal tip of the needle to a target of less than 90 mm2 at a distal end of the lumen on an unbroken wall of a blood vessel; a sensor attached to the guide the sensor configured to send a signal when a tip of a the needle passes a predetermined position within 4 mm the distal end of the lumen; and an indicator responsive to the signal and to produce signal visible to a practitioner through a skin of a subject.

According to some embodiments of the invention, the length of the guide is between 7 to 35 mm.

According to some embodiments of the invention, the guide has a lumen passing along the length of the guide, the lumen having a diameter between 1 to 7 mm.

According to some embodiments of the invention, the indicator is mounted on the guide.

According to some embodiments of the invention, the indicator is configured to be visible from outside through the skin under indoor fluorescent lighting.

According to some embodiments of the invention, the indicator is configured to be visible from a depth of at least 1 mm under the skin from outside through the skin under indoor fluorescent lighting.

According to some embodiments of the invention, the device further includes a vessel interface configured for connecting the guide to an unbroken outer wall of a blood vessel.

According to some embodiments of the invention, the vessel interface includes a suture hole.

According to some embodiments of the invention, the vessel interface has a concave surface fitting the outer wall of the vessel.

According to some embodiments of the invention, the lumen is surrounded on at least three sides by the vessel interface.

According to some embodiments of the invention, the lumen passes through the vessel interface.

According to some embodiments of the invention, the device further includes, a skin interface configured for attaching the guide to the skin.

According to some embodiments of the invention, a proximal end of the lumen is surrounded on at least three sides by the skin interface.

According to some embodiments of the invention, a proximal end of the lumen passes through the skin interface.

According to some embodiments of the invention, the sensor includes at least one of sensing a metal detector, a magnetic field detector, a light sensor, and a source.

According to some embodiments of the invention, the sensor includes an ultrasound emitter.

According to some embodiments of the invention, the sensor for measuring a blood flow parameter.

According to an aspect of some embodiments of the invention, there is provided a method of vascular access including: provide guide attached to an unbroken outer wall of a blood vessel, configured for guiding a needle from a skin surface to a target on the outer wall of the blood vessel; inserting the needle along the guide from the skin surface to the target; sensing when a tip of a the needle passes a predetermined position in the guide towards a lumen of the vessel; and indicating to a practitioner a result of the sensing.

According to some embodiments of the invention, the sensing is performed by a sensor mounted on the guide.

According to some embodiments of the invention, the method further includes activating an alarm when the needle tip retracts outward from the predetermined position towards the skin surface during the passing blood.

According to some embodiments of the invention, the method further includes: passing blood through the needle between the blood vessel and a dialysis device.

According to some embodiments of the invention, the method further includes: provide a second guide attached to the unbroken outer wall of the blood vessel, configured for guiding a second needle from the skin surface to a second target on the outer wall of the blood vessel; inserting the second needle along the guide from the skin surface to the target wherein the activating the alarm occurs the first second needle remains in the blood vessel while the first needle retracts outward.

According to some embodiments of the invention, the predetermined position is within 4 mm of a wall of the blood vessel.

According to some embodiments of the invention, the sensing includes at least one of sensing a metal object, sensing a magnetic field, sensing light reflected from the needle, and sensing a reduction of light blocked by the needle.

According to some embodiments of the invention, guide includes a plug of tissue, the method further including: inserting the tip of the needle through the plug.

According to some embodiments of the invention, the tissue includes vascularized tissue.

According to some embodiments of the invention, the method further includes: storing data on how long the needle tip was located inward of the predetermined position.

According to some embodiments of the invention, the storing is on a computer readable memory attached to the guide.

According to an aspect of some embodiments of the invention, there is provided a method of determining a status of a blood vessel including: providing a vascular access device permanently attached to fixed location on the blood vessel; aiming a sensor relative to the vascular access device; and measuring a parameter of the blood vessel at a predetermined location on the blood vessel with the sensor.

According to some embodiments of the invention, the method further includes: repeating the aiming and/or measuring after a time period of at least 1 hour.

According to some embodiments of the invention, the method further includes: repeating the aiming and/or measuring after a time period of at least 1 day.

According to some embodiments of the invention, the method further includes: actuating a signal on the blood vessel and measuring a propagation of the signal along the blood vessel.

According to some embodiments of the invention, the method further includes: waiting a predetermined period; repeating the measuring; and comparing a result of the measuring and the repeating the measuring to determine a change is the status of the blood vessel.

According to some embodiments of the invention, the method further includes: repeating the aiming previous to the repeating the measuring.

According to some embodiments of the invention, the sensor includes an ultra sound transducer, the method further including: estimating a blood flow velocity from a result of the measuring.

According to some embodiments of the invention, the sensor includes an optical sensor and the method further includes estimated a wall thickness of the blood vessel based on a result of the measuring.

According to some embodiments of the invention, the sensor includes a magnetic sensor and the method further includes estimated a blood flow velocity from a result of the measuring.

According to an aspect of some embodiments of the invention, there is provided a method of charging an implanted device including: providing at least two implanted vascular access devices located at different locations on a subject the two vascular access devices connected by an electrical conductor; applying a voltage differential across the at least two vascular access devices; passing a current along the electrical conductor between the at least two vascular access devices; and storing energy from the current in an implanted device.

According to some embodiments of the invention, the electrical potential difference between the at least two vascular access devices, is imposed on a skin of the subject.

According to some embodiments of the invention, the vascular access device includes: a needle insertion guide having a proximal end and a distal end; a vessel interface configured for attaching the distal end of the guide to a target on a blood vessel of a living subject; a skin interface configured for attaching the proximal end of the guide to a skin of the living subject.

According to some embodiments of the invention, the electrical conductor includes metal.

According to some embodiments of the invention, the electrical conductor includes a wire.

According to some embodiments of the invention, both of the at least two vascular access devices are attached to a single blood vessel.

According to some embodiments of the invention, a location of attachment of one of the at least two vascular access devices to the blood vessel is between 2 to 8 cm from a location of attachment of a second of the at least two vascular access devices to the blood vessel.

According to an aspect of some embodiments of the invention, there is provided an implanted system including: At least two vascular access devices connected by a metal conductor; a battery; a battery charging circuit conductively connected to the metal conductor for collected energy from an electrical potential difference between the at least two vascular access devices and charging the battery with the energy.

According to some embodiments of the invention, the vascular access device includes: a needle insertion guide having a proximal end and a distal end; a vessel interface configured for attaching the distal end of the guide to a target on an unbroken outer wall of a blood vessel of a living subject; a skin interface configured for attaching the proximal end of the guide to a skin of the living subject.

According to some embodiments of the invention, the metal conductor includes a wire.

According to some embodiments of the invention, a length of the metal conductor is between 2 to 8 cm.

According to an aspect of some embodiments of the invention, there is provided a system for vascular access including at least two implanted vascular access devices located at different locations; an implanted central control unit hard wired to each of the at least two vascular access devices wherein a minimum distance between the at least two vascular access devices is at least 2 cm.

According to some embodiments of the invention, each vascular access device includes a needle guide; a vessel interface for attaching one end of the needle guide to a blood vessel and a skin interface for attaching another end of the guide to a skin of a subject.

According to some embodiments of the invention, the system further includes: at least one of a computer readable memory, a human detectable indicator and a wireless communication device in data communication with the central control unit.

According to some embodiments of the invention, the system further includes at least one human detectable indicator positioned under a skin of the subject.

According to some embodiments of the invention, the system further includes: at least one sensor on each vascular access device in communication with the central control unit.

According to some embodiments of the invention, the system further includes at least one sensor mounted on each of the at least two vascular access devices, each at least one sensor in communication with the central control unit.

According to some embodiments of the invention, the vascular access device includes: a needle insertion guide having a proximal end and a distal end; a vessel interface configured for attaching the distal end of the guide to a target on an unbroken outer wall of a blood vessel of a living subject; a skin interface configured for attaching the proximal end of the guide to a skin of the living subject.

According to an aspect of some embodiments of the invention, there is provided a device for access to a blood vessel including: a needle insertion guide having a proximal end and a distal end; the guide including a track limiting an angle of needle insertion along the track from the proximal end to the distal end thereof; a vessel interface configured for connecting the guide to a target on an unbroken outer wall of a blood vessel; a flexible joint attaching the distal end of the guide the vessel interface and allowing the guide to flexible joint at least 15 degrees with respect to the interface.

According to some embodiments of the invention, an area of the target is less than 150 mm2.

According to some embodiments of the invention, an area of the target is less than 90 mm2.

According to some embodiments of the invention, an area of the target is less than 30 mm2.

According to some embodiments of the invention, the guide limits a direction of the needle to within 10 degrees of an angle of the needle guide.

According to some embodiments of the invention, the guide is cylindrical.

According to some embodiments of the invention, the guide has an average outer width of between 3 to 10 mm.

According to some embodiments of the invention, the guide has a lumen with an average inner width of between 2 to 7 mm.

According to some embodiments of the invention, the guide has a length of between 4 to 12 mm.

According to some embodiments of the invention, the flexible joint allows a rotation of the track with respect to the target of 15 degrees with a torque of less than 100 g cm.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

As will be appreciated by one skilled in the art, aspects of the present disclosure may be embodied as a system, method or computer program product. Accordingly, aspects of the present disclosure may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, some embodiments of the present disclosure may take the form of a computer program product embodied in one or more computer readable medium(s) having computer readable program code embodied thereon. Implementation of the method and/or system of some embodiments of the disclosure can involve performing and/or completing selected tasks manually, automatically, or a combination thereof. Moreover, according to actual instrumentation and equipment of some embodiments of methods, systems, and/or computer program products of the present disclosure, several selected tasks could be implemented by hardware, by software or by firmware and/or by a combination thereof, e.g., using an operating system.

For example, hardware for performing selected tasks according to some embodiments of the present disclosure could be implemented as a chip or a circuit. As software, selected tasks according to some embodiments of the present disclosure could be implemented as a plurality of software instructions being executed by a computer using any suitable operating system. In an exemplary embodiment, one or more tasks according to some exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

Any combination of one or more computer readable medium(s) may be utilized for some embodiments. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium and/or data used thereby may be transmitted using any appropriate medium, including but not limited to wireless, wireline, optical fiber cable, RF, etc., or any suitable combination of the foregoing.

Computer program code for carrying out operations for some embodiments of the present disclosure may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Some embodiments of the present disclosure may be described below with reference to flowchart illustrations and/or block diagrams of methods, apparatus (systems) and computer program products. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

BRIEF DESCRIPTION OF THE SEVERAL VIEWS OF THE DRAWING(S)

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

DESCRIPTION OF SPECIFIC EMBODIMENTS OF THE INVENTION

Figure 1A:
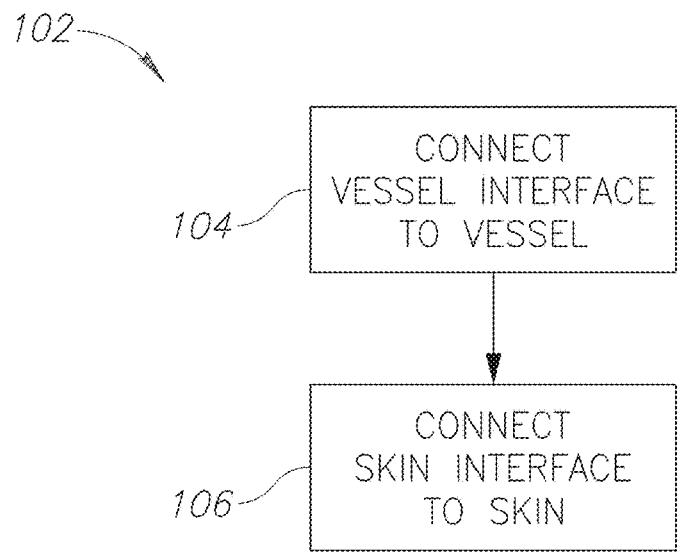
FIG. 1A is a flow chart illustrate of a method of installing a vascular access device VAD in accordance with an embodiment of the current invention.

The present invention, in some embodiments thereof, relates to a vascular access system and, more particularly, but not exclusively, to a system for facilitating access to a blood vessel and monitoring the access.

Overview

An aspect of some embodiments of the current invention relates system for detecting a position of a needle tip passing through a guide from a skin surface to a target on a wall of a blood vessel. Optionally, the system includes a sensor attached to the guide and/or an operator detectable indicator. For example, the sensor may signal when the needle point is positioned in a predetermined zone. Optionally, the indicator is operationally connected to the sensor and/or triggered by the signal of the sensor. In some embodiments, the guide and the sensor may be implanted into a human subject. Optionally the indicator is attached to the guide and/or implanted into the subject.

In some embodiments, the indicator is configured to signal when the needle reaches a zone near (for example within 4 mm of) the wall of the blood vessel. For example, during needle insertion the indicator may warn the operator that the needle has penetrated the vessel and/or that further insertion of the needle beyond a predetermined safe distance may risk puncturing a back wall of the vessel. Additionally or alternatively, the indicator may warn the operator when the needle point has left the vessel (e.g. retracted out of the vessel) and/or is in danger of leaving the vessel, for example during a treatment procedure.

In some embodiments, the guide may be connected by an interface to a skin of the subject and/or to the wall of the vessel. For example, a lumen of the guide may pass though one or both of the interfaces. For example, a distal end of the lumen may pass through the vessel interface and/or a proximal end of the lumen may pass through the skin interface. The interface optionally includes suture holes for suturing to the skin and/or blood vessel. Optionally one or both of the interfaces may protect the blood vessel and/or nearby tissue from puncture by the needle. Optionally the skin interface may help a clinician determine the angle of the guide (for example where the skin is flexible and/or it is difficult to determine the direction of the VAD from the skin).

In some embodiments, data is collected and/or stored regarding how much time the needle remains inside the vessel. For example, the sensor may be connected to an implanted computer readable memory and/or real time clock that stores data on time of needle placement. Alternatively or additionally, the time that the needle is in the vessel may be transmitted to an external processor and/or stored in an external memory and/or transmitted over a network. For example, the system may include an implanted wireless transmitter and/or an implanted power source.

An aspect of some embodiments of the current invention relates to a system for detecting condition of a blood vessel based on a one or more sensors and/or one or more markers in long term attachment to the vessel. For example, the markers may include a vascular access device. Optionally, measurements may be made periodically and/or used to track changes in the status of the vessel.

In some embodiments, an active sensor (e.g. a sensor and/or an actuator where the sensor detects changes in a signal created by the actuator and/or wherein the changes reflect something about the tissue between the sensor and the actuator) may be permanently attached to the marker. For example, a light source and/or an optical sensor may be attached to a vascular access device. Optionally, the spreading of light through a vessel will be measured and interpreted to estimate the maturity, growth and/or condition of a blood vessel, for example the thickness of a wall of the vessel.

In some embodiments, a small implanted ultrasound probe may be attached to a vascular access device. For example, the ultrasound probe will produce a wave that will enable measuring of blood flow parameters inside the vessel. Optionally the probe will include a sensor. For example, the sensor may measure echoes of the wave. Optionally data from the sensor will be sent wirelessly to an operator. Alternatively or additionally, the probe may send a wave and/or an external sensor may be used to measure an echo.

In some embodiments, the marker may be used to temporarily position the sensor during measurement. For example, an ultrasonic sensor may be aimed (e.g. positioned and/or oriented) with respect to one or more vascular access devices in order to get a preferred positioning with respect to the vessel and/or to get a consistent positioning for measurements repeated over time and/or to make measurements of the same section of a blood vessel over time.

In some embodiments, more than one marker may be used to facilitate a measurement. For example, two markers may be used to measure a condition and/or occurrence between the markers. For example, an actuator may be placed near an upstream marker and/or a sensor at a downstream marker to measure the transmission of the actuated signal along the vessel.

An aspect of some embodiments of the current invention relates to a system of vascular access and/or sensing. For example, the system may include multiple integrated components including one or more implanted vascular access devices and/or an implanted controller and/or one or more implanted sensors and/or one or more external sensors and/or an external controller and/or an internal power source and/or an external power source and/or an implanted actuator and/or an external actuator and/or an implanted indicator and/or an external indicator. Optionally the fixed VAD are used to facilitate repeated measurements in the same location and/or over a known portion of the vessel and/or body. For example, a VAD may be used a marker to position an external sensor. Alternatively or additionally, a signal may be generated at a VAD and measured outside the VAD to diagnose tissue around the VAD. Alternatively or additionally, changes in a signal may be measured as the signal propagates from one VAD to another. Alternatively or additionally, a VAD may be used an access point for inserting a device into the vessel and/or other locations in the body.

In some embodiments treatment is performed through two blood lines recirculating blood from and/or to a blood vessel. For example, such recirculating may be used in hemodialysis. For example, a fistula and/or a graft and/or catheter recirculating the blood back to the vessel. From example, each line accesses the vessel through a needle passing through the outer skin of the subject to the vessel. The patient's blood is optionally passed across a dialysis membrane. An implanted vascular access device (VAD) can be designed to guide safely a needle to enter the vessel in a predetermined location, orientation and/or distance. For example, a VAD may include a 5 mm-diameter cylindrical conduit whose wall is made of porous material that is placed by a surgeon from under the skin to the outer wall of a vessel. Its length when implanted in the upper arm may range for example between 5 to 35 mm. Optionally the VAD includes two footplates that enable suturing it to the dermis and/or to the blood vessel. The VAD optionally has an internal valve. For example, the valve may stop back bleeding. Alternatively or additionally, the device may not include a valve.

In some embodiments, a dialysis needle's length varies between a standard 25 mm to 31 mm Stainless Steel (SS) needle and/or between 25 mm to 38 mm for a plastic needle and/or a catheter for example a plastic catheter as long as 100 mm. The plastic needle may include a metal inserter. In some embodiments, the plastic needle is more expensive than a SS needle. Optionally, various embodiments of VADs may have sizes and/or lengths to fit various sizes of the needles. A VAD may work with a sharp needle and/or with a blunt needle. In some embodiments, the design allows for a sharp needle that is shorter than a blunt need by the bevel's 5 mm length. Alternatively or additionally, the design covers blunt needles that may be 5 mm longer. For example, there may be two sizes of VADs. The first optionally is configured for a 25 mm needle and the second is optionally configured for a 31 mm needle. The VAD for the 25 mm needle will optionally cover vessels that are in the depth range of 5-8.5 mm. The VAD for the 31 mm needle will optionally cover the depth range of 8.5-12 mm. In some embodiments, a VAD will be configured to reach deeper vessels and/or fit longer needles.

In some embodiments, a permanent implant for accessing a vessel in dialysis may further incorporate sensing and/or data gathering. The data gathering optionally increases the value that this implant gives to its customers. Data may be collected from the sensors and/or from the treatment statistics. In some embodiments, the data help monitoring of care.

The electronic embodiments that are described below may be applicable to any needle guide apparatus. Moreover, they might be applicable, in whole or in part, to any vascular access device. In a broader view, implanted sensors and data management tools may promote care in various implants that are used in a variety of medical areas. For instance, the sensors may be used to monitor implanted joints (hip or knee, etc.) and/or grafts.

An aspect of some embodiments of the current invention relates to an implanted vascular access device configured to encourage ingrowth into the access channel of native tissue of a particular type and/or geometry. For example, tissue growing into a VAD and/or along one or more sides of the VAD may help prevent infection and/or back bleeding and/or blockage of the VAD. For example, the VAD may be configured to encourage the growth of a particular tissue type along a wall of a guide and/or inside a lumen of a guide.

An aspect of some embodiments of the current invention relates to a skin access to an implanted vascular access device.

An aspect of some embodiments of the current invention relates to a connection between a vascular access device and a blood vessel that allows flattening of an access needle with limited deformation of the vessel.

An aspect of some embodiments of the current invention relates to a vascular access device providing access to a native blood vessel. For example, a VAD may be used to access a central vein (for example for dialysis) and/or a central artery (for example for repetitive treatments that require access to a large artery, for example for treatment of blood disease and/or for chemotherapy.

The benefits from the sensors readings, either online or over time, will be conjugated to the sensors and probably to the VAD (or at least to a permanent implant). This will include trend analysis indication on a change in light pattern that might be analogues to change in vessel wall thickness and/or a change in vessel wall movement that might be analogous to a change in blood pressure, or an occlusion within the blood vessel, etc.

In some embodiments, the known locations of one or more VADs on the blood vessel may be used to measure changes to the vessel and/or its hemodynamics. For example, blood velocity and/or capacity etc. between points may be measured.

In some embodiments, a light on a VAD is reflected into the blood vessel and/or used to determine changes in wall thickness of the vessel. In some embodiments, wall thickness is an important indicator of maturity (usefulness) of fistula In some embodiments, a sensor will detect when needle penetrates a blood vessel and/or facilitated prevention of backwall perforation.

In some embodiments data will be stored on the implant. The data will optionally be available to clinicians even when the patient he moves from clinic to clinic.

EMBODIMENTS

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

FIG. 1A is a flow chart illustrate of a method of installing a vascular access device in accordance with an embodiment of the current invention. In some embodiments an access device includes a vessel interface and/or a skin interface connected by a track. Optionally, the vessel interface is connected 106 to a blood vessel (for example by suturing to the vessel wall) and/or the skin interface is connected 104 to a skin (for example by suturing to the dermis). Optionally, the skin interface holds the head of the track visible and/or accessible from the skin surface and/or the vessel interface holds the foot of the track to the vessel. For example, when a needle tip enters the track at the skin surface and/or is advanced along the track, the track guides the needle tip to a target region of the vessel wall near the vessel interface. For example, the connection region may be an area of 0.1 to 0.25 mm and/or between 0.25 to 1 mm and/or between 1 to 5 mm and/or between 5 to 15 mm and/or between 15 to 25 mm. Optionally, device including the vessel interface remain outside the wall of the blood vessel. For example, the vessel wall retains its integrity and/or the inner surface of the vessel is native tissue. Optionally, the track, residing on the outside wall of the vessel, simply guides a needle from an opening in the skin and into the vessel lumen.

Figure 1B:
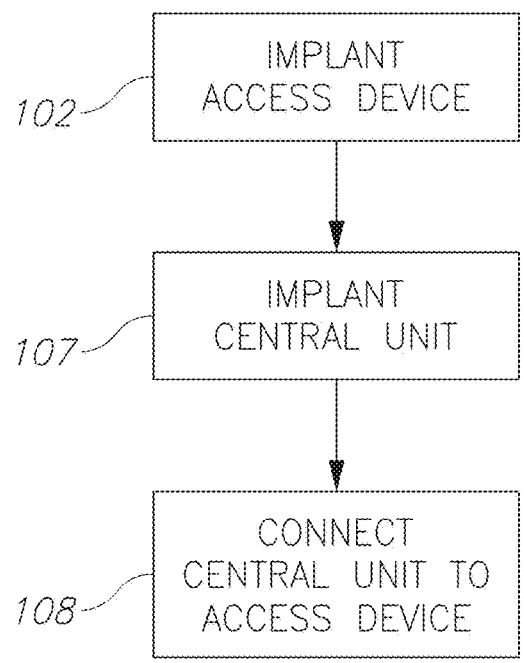
FIG. 1B is a flowchart illustration of a method of installing a vascular access system in accordance with an embodiment of the current invention.

FIG. 1B is a flowchart illustration of a method of installing a vascular access system in accordance with an embodiment of the current invention. Optionally, a vascular access device may include active components, for example electronic components. Optionally, some or all of the active components may be connected to a central unit. In some embodiment, multiple access devices may be connected to a single central unit. For example, the central unit may facilitate coordination between active components on different access devices and/or facilitate use of a single active component by multiple access devices. For example, active components may include a sensor and/or a communication device and/or a human interface (for example an input interface and/or an output interface for example an indicator) and/or an actuator and/or a power source and/or a processor.

In some embodiments, a central unit may be implanted 107 and/or an access device may be implanted 108 into a subject. Optionally the central unit and the vascular access device may include separate implantable units. Alternatively or additionally, a central unit may be physically associated with an access device and/or implanted with an access device as a single unit. Optionally, after implantation 102, 107 of the access device and/or the central unit, the access unit may be connected 108 to the access device. For example, a central unit will be connected 108 to a vascular access device by a wire.

In some embodiments, a central unit will supply power to multiple access devices. Additionally or alternatively, multiple access devices will serve as electrodes for charging a single power supply. In some embodiments, sensors and/or actuators on multiple access devices may be coordinated. For example, an upstream access device and a downstream device may be attached to a single blood vessel. A signal may be transmitted by one device and/or received by a coordinated sensor on the second device. For example, a magnetic signal may be transmitted at a fixed time by the upstream device, magnetizing blood at an upstream location. Optionally the downstream device will measure the residual magnetic signal as the magnetized blood is swept down the vessel. The coordinated data about the transmitted and detected signals may be processed to determine hemodynamics. Optionally, data may be stored internally and/or processing may be performed by an implanted processor. Alternatively or additionally, data may be stored internally and retrieved and processed later by an external processor. Alternatively or additionally, data may be transmitted by an implanted transmitter to an external memory and/or processor.

In some embodiments, an access device may be connected to an implanted blood vessel (for example a fistula). Optionally, an access device and/or a central unit may be implanted at the same time as a graft and/or a fistula. Alternatively or additionally, the access device may be implanted with the fistula and/or the central unit may be implanted later. Alternatively or additionally, the central unit may be implanted with the fistula and/or the access device may be implanted later. For example, an access device may be implanted while the fistula is maturing and/or after the fistula matures and/or after a fistula is already in use (for example in response to an event.

In some embodiments, all parts of a vascular access system may be implanted together. For example, one or more access devices and a central unit may be implanted all at once and/or connected at the time of implantation. For example, in a patient with high risk of access problems, a full access system may be implanted with a graft and/or a fistula. Alternatively or additionally, one or more components may be implanted at one time and/or further components may be implanted and/or interconnected later.

In some embodiments, a vascular access system will include multiple interconnected components and/or separately implanted components. For example, multiple access devices may be powered by a single power source. Optionally, the power source may be internal to one of the access units and/or the power source may be implanted in a central unit. For example, different units may be connected by wires. Alternatively or additionally, an access unit may include a simple non-powered guide without electronic components. In some embodiments, an access unit may include a sensor and/or an indicator. Alternatively or additionally, multiple access units may share an indicator. For example, a sensor on an individual access unit may determine a needle position along the guide of the access unit. A shared indicator may indicate to a user when a needle reaches a blood vessel and/or exits a blood vessel along either of the units.

Figure 2A:
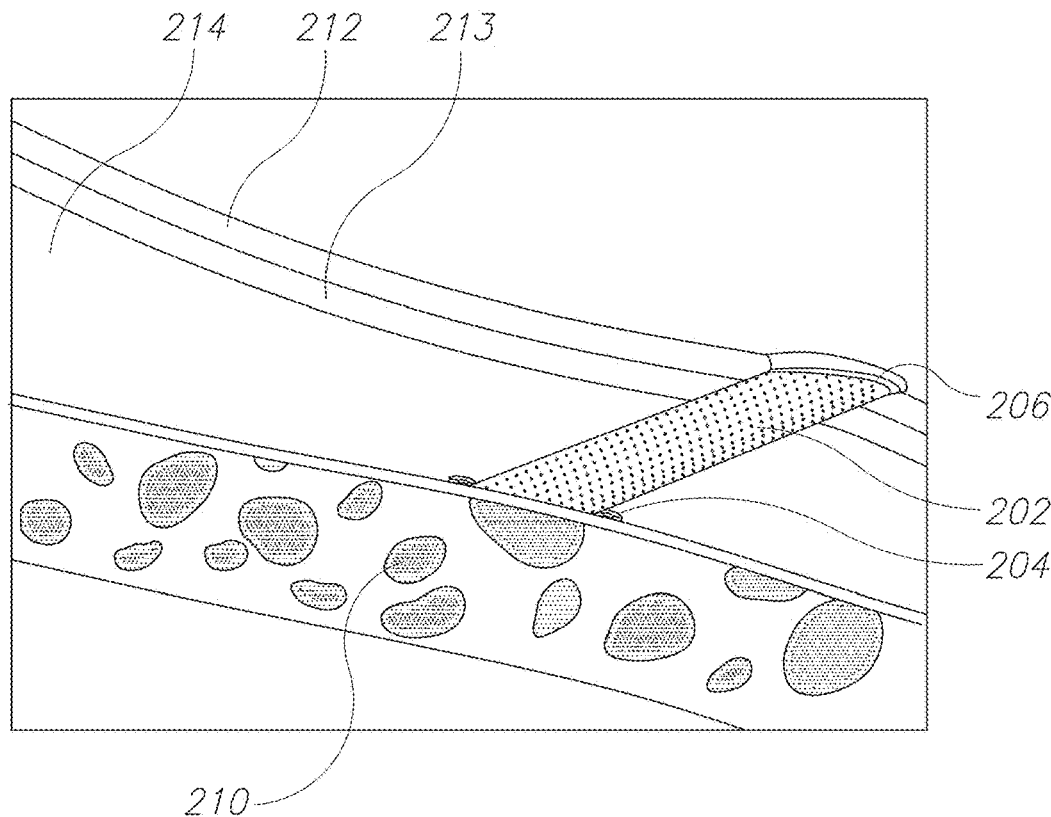
FIG. 2A is a schematic illustration of a vascular access device attached to a subject in accordance with an embodiment of the current invention.

FIG. 2A is a schematic illustration of a vascular access device attached to a subject in accordance with an embodiment of the current invention. In some embodiments, a vascular access device includes a needle guide 202 and/or a skin interface 206 and/or a blood vessel interface 204. For example, guide 202 may include a cylindrical tube. Optionally the tube is configured to encourage ingrowth of a particular kind of native tissue, for example vascular tissue and/or the tube is configured to discourage ingrowth of a particular kind of native tissue, for example scar tissue.

In some embodiments, tissue growth will give the VAD characteristics close to a natural blood vessels and/or body lumen. In some embodiments this helps fighting infections. Alternatively or additionally, native tissue (for example vascular tissue) inside the VAD may act like a plug to prevent backflow bleeding. Optionally, the tissue will prevent back bleeding without blocking a lumen for needle insertion.

In some embodiments, a skin interface 204 is attached to an epidermis 212 and/or a dermis 213. For example, attachment may be by means of suturing and/or adhesive and/or staples and/or clamps. Alternatively or additionally, a skin interface may be attached to deeper subcutaneous tissue 214. In some embodiments, a vessel interface 204 may be attached to the wall of a blood vessel 210. For example, attachment may be by means of suturing and/or adhesive and/or staples and/or clamps. In some embodiments, the shape of the skin interface might be flat or might be in any other geometry, for instance, a half-dome. Optionally the edges of the skin interface are deep inside the body to avoid skin erosion with the edge when the skin suffers from a hit. Optionally, a half-dome will also enable more skin area to be thick enough to enable good blood perfusion to prevent necrosis.

In some embodiments, an access device is designed to guide a needle to a target area on a wall of a blood vessel 210. Optionally, the access device itself does not interrupt the integrity of the vessel wall. For example, the access device may be placed on the outside of the vessel wall. For example, no element of the device may be placed inside the lumen of the blood vessel. Optionally, be residing on the outside wall of the vessel, in some embodiments, avoiding parts residing in the vessel may help avoiding some causes of failure, for example infection and/or reduction in the viability of the vessel.

An access device may have various sizes and shapes. For example, a shape or size of the vascular access device may be configured to a particular size and/or kind of needle. For example, the length of a guide of the access device may range between 90% to 80%, and/or between 80% to 60% and/or between 60% to 20% the length of a dialysis needle. For example, the guide of an access device may include a hollow channel with an inner width of ranging between 110% to 130% and/or between 130% to 180% and/or between 180% to 300% the outer diameter of a dialysis needle. In some embodiments, portions of the channel may be wider than the above width. A dialysis needle's length may vary for example between the standard 15 to 32 mm for a metal cannula and/or between 25 to 38 mm for a plastic cannula. A dialysis needle may range from example from 14 to 18 gauge e.g. from 1 to 2.5 mm outer diameter and/or between 0.8 to 2.0 inner diameter. Optionally a plastic needle may include a metal introducer needle and/or a plastic cannula. Optionally, there may be different sizes and/or lengths of the guide of the access device. For example, each size may fit a particular size of dialysis stainless steel needles and/or plastic needle.

Figure 2B:
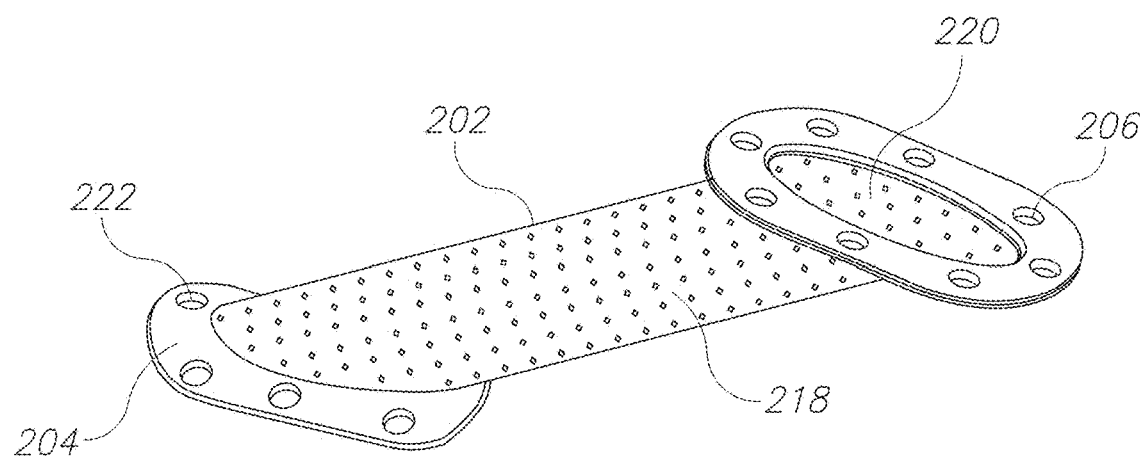
FIG. 2B is a schematic illustration of a vascular access device in accordance with an embodiment of the current invention.

FIG. 2B is a schematic illustration of a vascular access device in accordance with an embodiment of the current invention. In some embodiments, a guide 202 of an access device may include a cylindrical channel. Optionally walls of the cylindrical channel include perforations 218. For example, perforations may facilitate tissue ingrowth. In some embodiments a vessel interface 204 may include a curved plate. For example, the plate may be curved to match a shape of a wall of a blood vessel. Optionally the interface 204 includes suture holes 222 to facilitate suturing to the blood vessel.

Figure 2C:
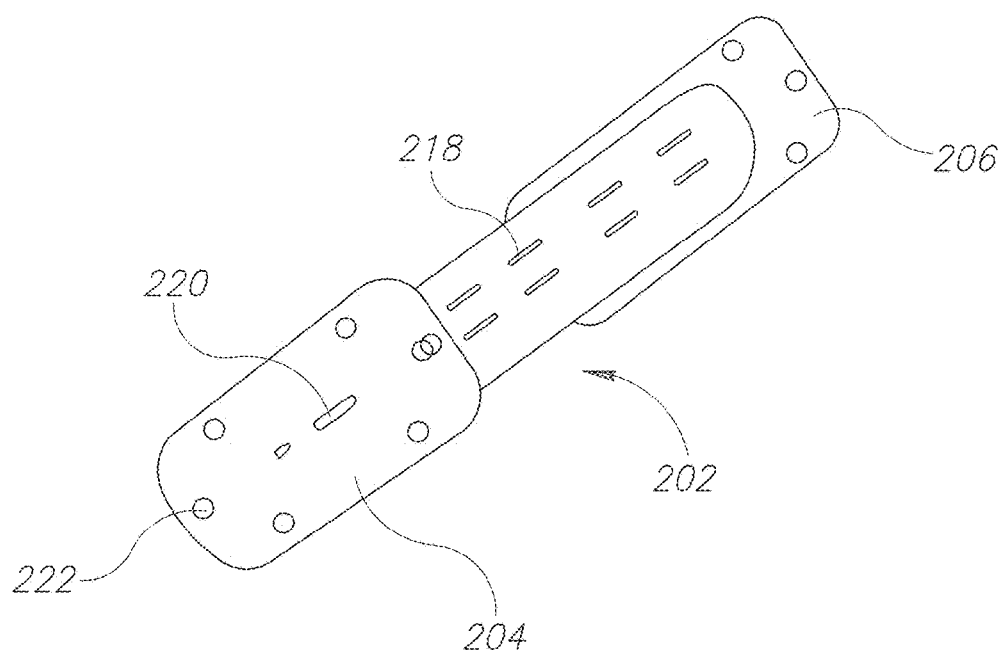
FIG. 2C is an image of a vascular access device in accordance with an embodiment of the current invention.

FIG. 2C is an image of a vascular access device in accordance with an embodiment of the current invention. In some embodiments, a vascular access device may include a guide 202, a vessel interface 204 and a skin interface 206. Optionally, the device may be a passive mechanical device without moving parts and/or without electronic parts. Optionally, the guide includes a lumen 220 through which a needle passes from a skin surface to a target region on the blood vessel. Optionally, the guide 202 is perforated with one or more perforations 218. Optionally, perforations 218 and/or lumen 220 are sized and shaped to encourage growth of a preferred tissue along lumen 220.

In some embodiments, the shape and/or flexibility of the device may affect dynamic processes. For example, a passive guide may have a changing geometry which may affect needle insertion differently at different stages of insertion. For example, a lumen may have a narrow waist which resists forward movement of a plastic cannula when an introducer has entered far enough into a blood vessel. Once the introducer is removed, the cannula may be flexible enough to enter the vessel. Alternatively or additionally, the walls of the guide may be elastic, initially resisting further movement of the introducer (alerting the operator that the introducer has entered the vessel, but allowing subsequent movement into the vessel. Elasticity of the guide may also be used to prevent back bleeding. For example, once a cannula is removed from the guide, the guide may contract around its lumen closing back the lumen (for example by compressing tissue that has ingrown into the lumen. Alternatively or additionally, the lumen may have areas of changing width and/or shape to encourage growth of tissue of different kinds and/or rates and/or densities at different points along the lumen. Alternatively or additionally, the positions of perforations along the guide may be coordinated with the positions shape of the lumen.

In some embodiments, a small internal skirt on the inside lumen of a guide near its attachment to the blood vessel will be designed to stop a standard dialysis needle before the needle reaches the vessel. Optionally this feature, together with other design features of the access needle, will help avoid back wall perforation. In some embodiments, the skirt position might be altered remotely during specific stages of the procedure. For instance, skirt seals the lumen when there is no needle in the guide and opens after a sensor indicates that a needle is approaching it.

Figure 2D:
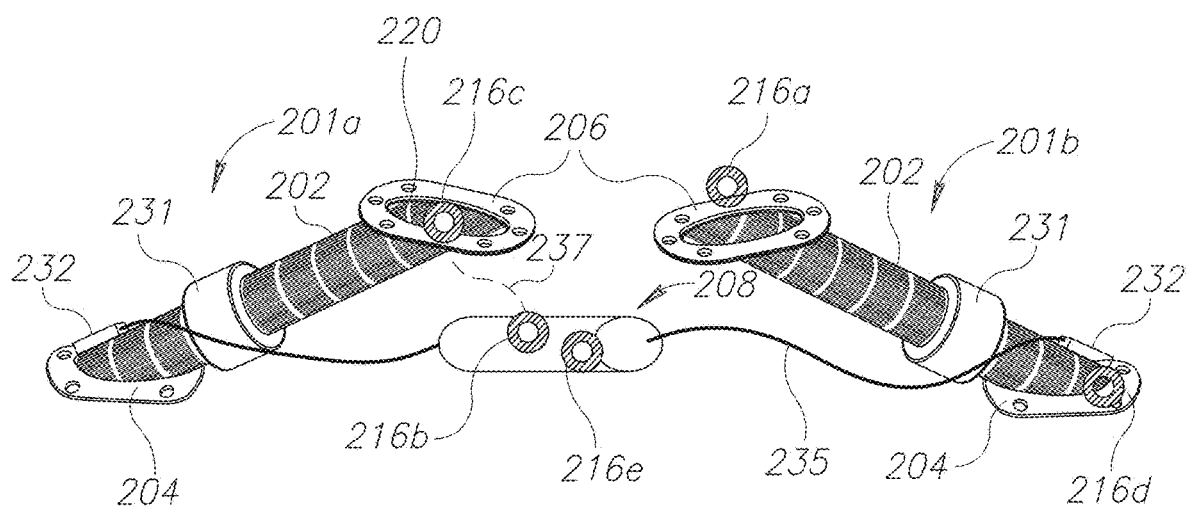
FIG. 2D is a schematic illustration of a vascular access system in accordance with an embodiment of the current invention.
Figure 10:
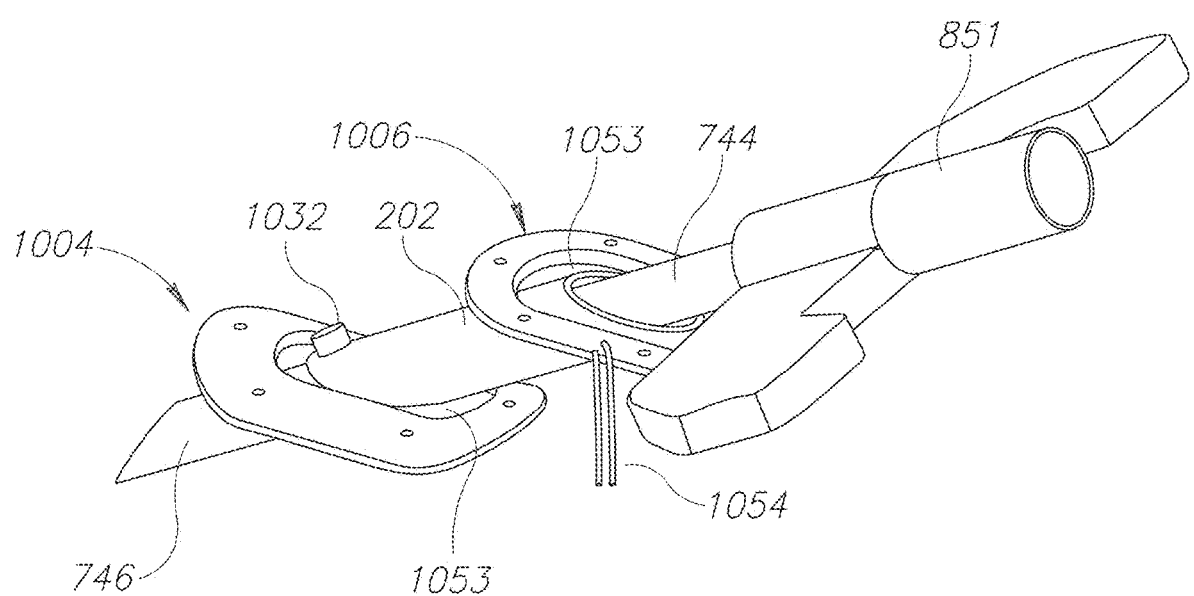
FIG. 10 is a schematic illustration of a vascular access device with a flexible footplate in accordance with an embodiment of the current invention.

FIG. 2D is a schematic illustration of a vascular access system in accordance with an embodiment of the current invention. In some embodiments, a vascular access system may include active components. Optionally, a vascular access system may include active electronic components, including for example a sensor, an actuator, an indicator, a user interface, a power source, and/or a transceiver. Alternatively or additionally, a vascular access system may include a moving hinge may connect between a vessel interface and a guide (for example as illustrated in FIG. 10).

In some embodiments, some or all active electronic components may be housed in an implant will be housed in an enclosure. Optionally, the enclosure may be rigidly attached to a VAD. Alternatively or additionally, an implanted electronic connection box will be connected with one or more wires to a VAD. In some embodiments, the electronic connection box may move of its orientation of location relative to the VAD. Optionally the dimensions of the electronic connection box may range between 1 mm to 5 mm and/or between 5 mm to 15 mm and/or between 15 mm to 30 mm and/or between 30 mm to 100 mm. Optionally the electronic connection box is implanted into the subject.

In some embodiments a system may include more than one VAD 201a, 201b. For example, for hemodialysis one VAD may be used for extracting blood and another for returning the blood. Optionally, both VAD's 201a, 201b are installed on a single blood vessel. For example, the VAD's 201a, 201b may be installed on an Arteriovenous (AV) fistula. In some embodiments the VAD's 201a, 201b may be installed in a retrograde configuration (both VAD's in the opposite directions). Alternatively or additionally VAD's 201a, 201b may be installed in an antegrade configuration (both VAD's in the same direction) and/or in non-similar angles.

In some embodiments, a system may include two VAD's 201a, 201b and one electronic connection box 208. In some embodiments, one or more sensors 232 may be rigidly attached to a VAD 201a, 201b and/or to a connections box 208 and/or may be connected moveable connected to a VAD 201a, 201b and/or to a connections box 208 (for example by a wire 235). In some embodiments, a VAD 201a, 201b may include a permanently connected sensor and/or indicator. Alternatively or additionally, a sensor and/or an indicator may be added to a VAD 201a, 201b and/or connection box 208 before and/or after the implantation. Optionally, the VADs 201a and/or 201b and/or the connection box 208 may be implanted and/or suturing individually. Optionally, the VAD and/or the connection box 208 may be interconnected, for example by a wire 235.

In some embodiments, a system may include a single indicator and/or multiple indicators. For example, a single indicator 216e on the connection box 208 and/or on one of the VADs may indicate to an operator may a needle tip is approaching a wall of a blood vessel along a guide 202 of either of the VAD 201a, 201b. Alternatively or additionally, a VAD may have its own indicator 216a, 216d. For example, an indicator 216a and/or 216d on VAD 201b may indicate when the needle tip is approaching a blood vessel wall along guide 202 of VAD 201b and/or an indicator on VAD 201b may indicate when the needle tip is approaching a blood vessel wall along guide 202 of VAD 201b. In some embodiments, the connection box has two plugs that enable connecting the box 208 independently to two VADs 201a, 201b. In some embodiments, sensors may be placed in different locations on the VAD according to their functionality, for instance, emitter and receiver. Optionally an indicator (e.g. indicator 216a-216e) may be configured to be seen through skin. Optionally the color and/or power of an LED will be configured to be easily seen through skin of a specific color and/or any color. Optionally, the indicator is configured to be seen at a depth of between 0 to 1 mm and/o between 1 mm to 5 mm and/or between 5 mm to 2 cm and/or between 2 to 5 cm. Optionally, the indicator is configured to show the direction and/or the orientation of the VAD within the body. For example, this may help the operator to advance a needle in a desired direction and orientation.

In some embodiments, a VAD includes sensing and data gathering capabilities. For example, a sensor 232 may be mounted on or near the vessel interface 206. For example, sensor 232 may be used to detect when a needle tip is approaching the vessel wall. Alternatively or additionally, a sensor and/or a set of one or more sensors and/or actuators may be used to monitor a condition of a subject (for example a condition of the blood vessel). Data that are collected from the sensors and from the treatment statistics may be used for monitoring the care of the subject. For example, data collected over time may be used to assess the progress of treatment and/or detect side effects. Optionally, data may be stored in a local memory and/or transmitted to a remote receiver. Some examples active components and/or their use that may be used in the system of FIG. 2D are described herein below in the description of FIG. 7A.

In in some embodiments, integration of implanted devices, sensor the electronic assists in medical assessment and/or operation. For example, an implanted sensor monitors and collects data on the activities that the implant was designed for. In some embodiments, there is a need to find a location for placement of electronic parts. For example, the VAD may be limited in its size and/or position in a manner that does not allow housing all of the sensors actuators and/or associated electronics in the VAD. These components may include electrical circuits, communication units, indicators and/or power sources.

In some embodiments, a VAD 201a, 201b includes a mechanism to prevent back bleeding. For example, a valve 231 may be provided. Alternatively or addition, back bleeding may be prevented by tissue that grows into the VAD 201a, 201b and/or be pressure put onto the blood vessel after needle removal and/or by an obturator and/or a balloon.

In some embodiments, an optical fiber 237 may be used to illuminate a VAD. For example, this would make it possible to locate an indicator 216c on the VAD 201a while the power supply and/or electronics remain on the connection box 208. Optionally the optical fiber 237 is made of silicone and/or is connected to a silicone component of the VAD. For example, the electronics and/or a light source 216b may be mounted inside the battery box and only the optical fiber is connected to the VAD. Optionally indicator 216c may be formed as a target for the location where the needle should be in inserted. For example, a silicon element (for example hinge cover 1053 of FIG. 10) may have the form of an illuminated a subdermal illuminated "ring" that surrounds the needle entrance of the VAD. Lights optionally for a line to indicated an orientation of the VAD. For example, flashing and/or sequentially illuminated lights may indicate an entrance location and/or a preferred needle orientation to a clinician before puncturing the skin.

Figure 3A:
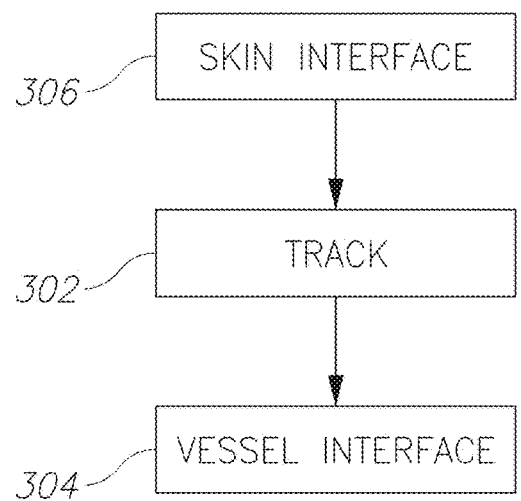
FIGS. 3A and 3B are block diagrams illustrating vascular access devices in accordance with some embodiments of the current invention.

FIG. 3A is a block diagram illustrating a passive VAD in accordance with an embodiment of the current invention. For example, a VAD may include a skin interface 306 that facilitates inserting a needle tip through a skin surface to a guide 304. For example, the skin interface 306 may attach a proximal opening of the guide track 302 to the skin surface. Optionally the guide track 302 includes a lumen directing the needle tip to a target area on a wall of a blood vessel. Optionally, the vessel interface 304 retains a distal opening of the guide track attached to the target area.

Figure 3B:
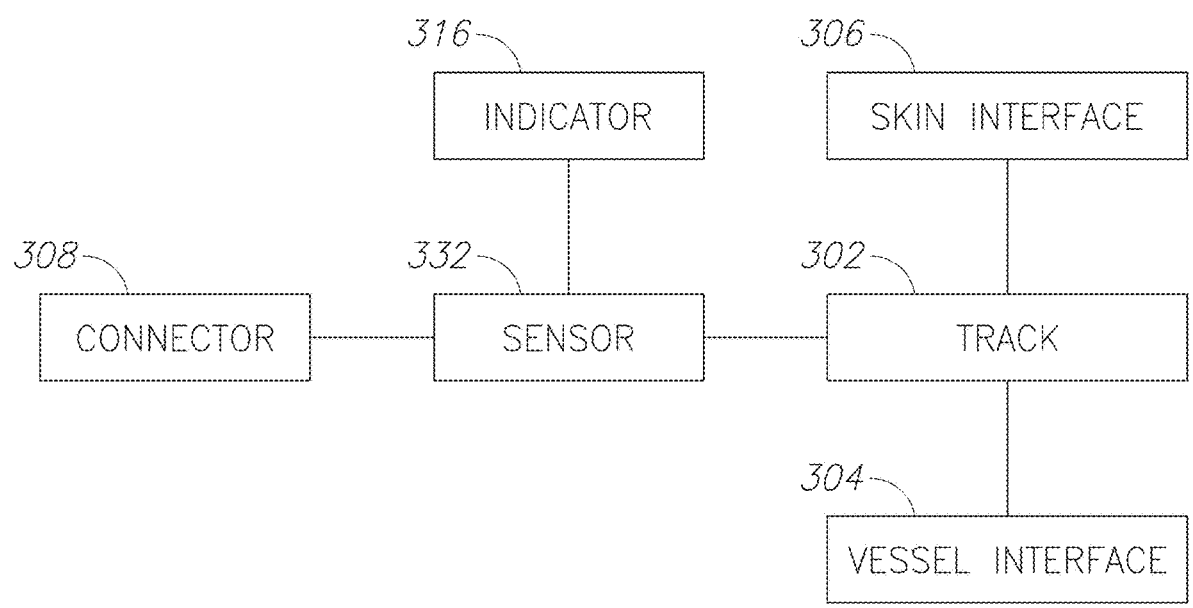

FIG. 3B is a block diagram illustrating an active vascular access system in accordance with some embodiments of the current invention. Optionally, an active system may include a passive VAD device with active components. For example, active components may include a sensor 332 (for example as illustrated herein above and/or below) and/or an indicator 316 (for example a light and/or vibrator and/or sound emitter) and/or a connector 308 (for example including a wire and/or an optical fiber)

Figure 3C:
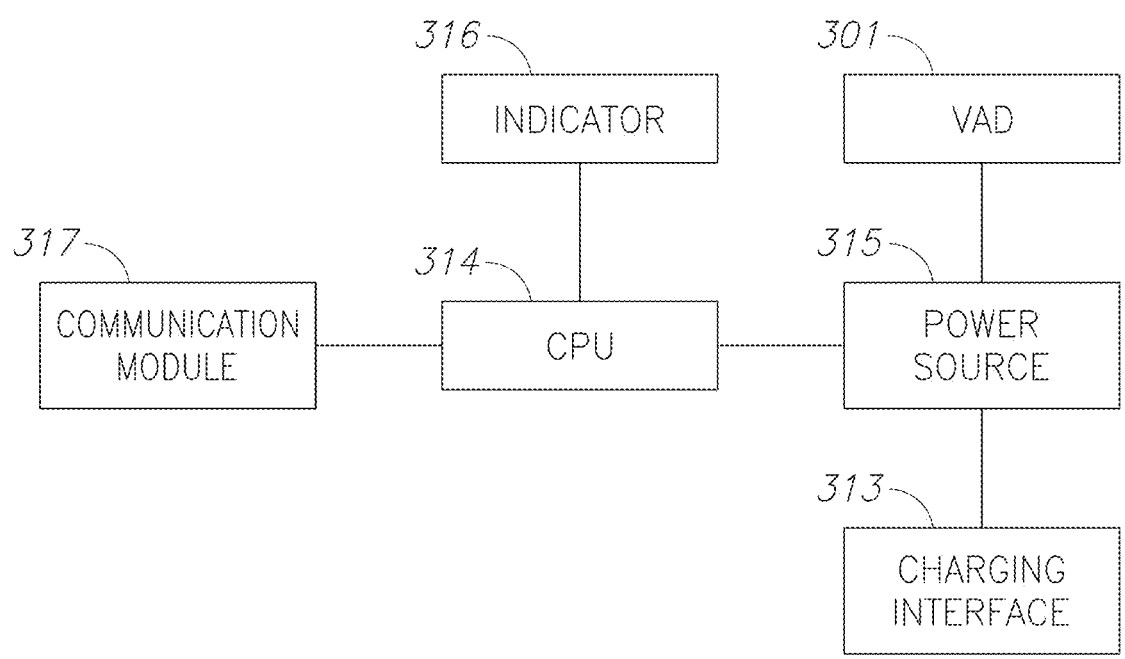
FIG. 3C is block diagram of vascular access systems in accordance with some embodiments of the current invention.

FIG. 3C is block diagram illustrating a vascular access system with multiple integrated components in accordance with some embodiments of the current invention. By the way of illustration, the present invention is described with connection to a vascular access device 301 for hemodialysis (for example as illustrated in any of the embodiments herein above or below). For example, Hemodialysis treatment is done through two needles (one for blood collection and one of blood return) that access a blood vessel—for example a fistula and/or a graft (in some embodiments a graft may include a blood vessel harvested from another location in the body of the subject, alternatively or additionally the graft may include a synthetic vessel, alternatively of additionally a graft may include a blood vessel grown from cells of the subject either in vivo and/or in vitro). Optionally each needle reaches the blood vessel from outside the subject's skin and/or passes along a guide of VAD 301 (for example through a tube). For example, the guide may include a 5 mm-diameter cylindrical conduit. Optionally the VAD is placed by a surgeon from under the skin to the outer wall of the blood vessel. For example, for a VAD implanted in the upper arm, the length of a VAD guide may range between 5 to 25 mm and it may have two interfaces for example for attachment to the dermis and/or to the blood vessel. In some embodiment of Hemodialysis, blood passing through the needles is for example passed across a dialysis membrane.

In some embodiment the system may include an active component (for example as illustrated in any of the embodiments herein above or below). For example, an active component may be attached to VAD 301 (for example to a skin interface and/or a vessel interface and/or a guide). Optionally or additionally, an active component may be located separate from the VAD. Optionally the active component may include a sensor 332 and/or an actuator and/or an indicator 316 and/or a power source 315 and/or a communication module 317 (e.g. a receiver and/or a transmitter), and/or a switch (for example a power switch for example a reed switch) and/or a power collection device (for example a charging interface e.g. an induction coil) and/or a processor 314. Optionally the active component may be rigidly attached to the VAD and/or attached to the VAD by a flexible connector, for example including a wire and/or an optical fiber. In some embodiments the system may include an external element, for example an external power source and/or an external controller and/or an external sensor and/or an external actuator and/or an external indicator (for example as illustrated in any of the embodiments herein above or below). For example, connection to the external element may be by means of the communication module 317 and/or the charging interface 313 and/or through an operator position the external element with respect to a VAD.

Figure 3D:
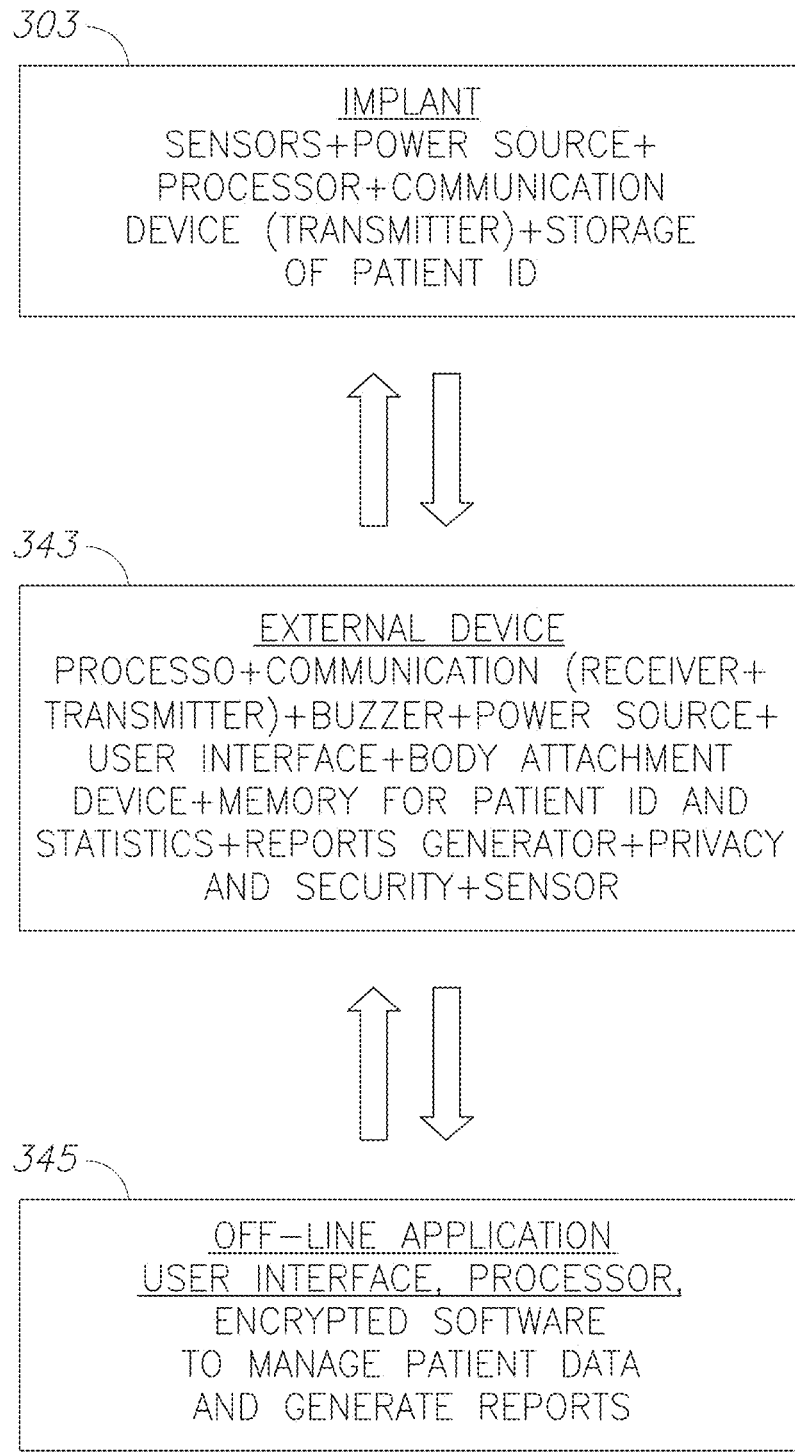
FIG. 3D is a block diagram illustrating a system for measuring changes in an internal structure in accordance with an embodiment of the current invention.

FIG. 3D is a block diagram illustrating a system for measuring changes in an internal structure in accordance with an embodiment of the current invention. In some embodiments, an implanted device 303 may have a fixed position with respect to an internal structure and/or the position of the implanted device 303 may be determinable from outside the subject. Optionally an external device 343 includes a sensor configured to measure an aspect of the structure and/or its functioning. Optionally the implant 303 is used to position the external device to measure the external structure in a reliable and/or repeatable manner. For example, the external device 343 is positioned in relation to the insert 303. In some embodiments, data may be processed by the external device 343 and/or by the implant 303 and/or by an off-line application 345. For example, the internal structure may include a blood vessel and/or the implant 303 may include one or more VADs.

In some embodiments, a vascular access and care system may include an implanted system 303 of implanted components (for example including a sensor and/or a power source (for example a battery) and/or a processor (optionally with data encryption) and/or a communication device (for example a transceiver) and/or a computer readable storage (for example for a Patient ID). For example, embodiments of a systems of implanted components are described as with respect to FIGS. 2A-2D and/or 3A-3C herein above. Optionally, an external device 343 of a vascular access and care system may also comprise a power source and/or a processor (optionally with data encryption) and/or a communication device (for example a transceiver) and/or a computer readable storage (for example for a Patient ID and/or patient statistics) and/or a report generator and/or a privacy and security module and/or a user interface and/or a sensor and/or a body attachment device (for example the external device may be wearable). Optionally an external device 343 may include an external sensor (for example a blood velocity meter as described for example in connection to FIGS. 11A and/or 11B). Alternatively or additionally, an external device may include an external controller and/or a charger (for example as described in FIG. 13A and/or FIG. 13B). In some embodiments, a vascular access and care system may include off line components 345. For example, offline components 345 may include a processor and/or a user interface and/or encrypted data and/or software to manage patient data and generate reports.

Figure 3E:
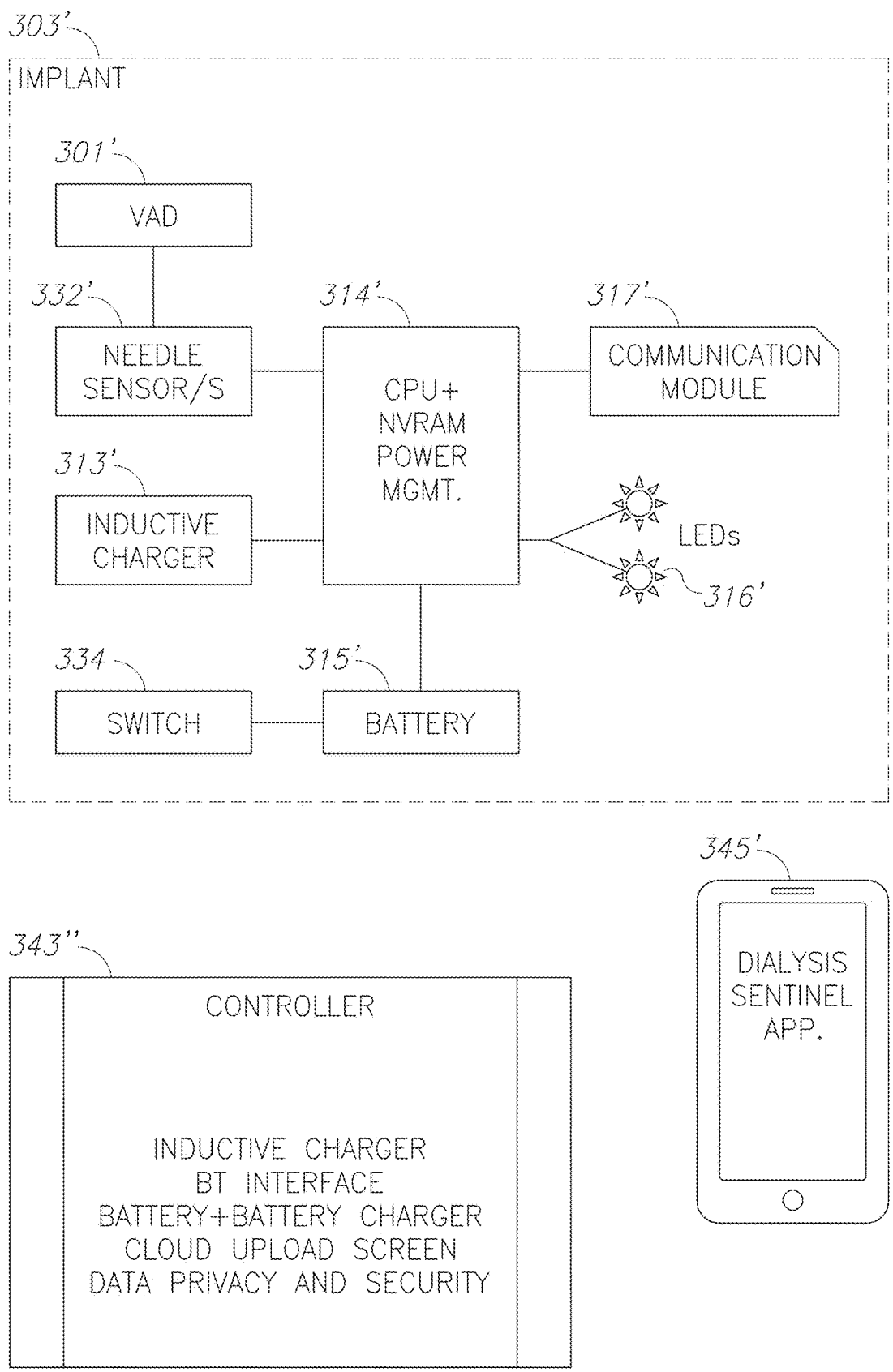
FIG. 3E is a schematic illustration of a vascular access and care system in accordance with an embodiment of the current invention.

FIG. 3E is a schematic illustration of a vascular access and care system in accordance with an embodiment of the current invention. In some embodiments, a vascular access and care system may include an implanted VAD 301' and/or active implanted components and/or an external controller 343'. For example, an external controller 343' may connect wirelessly to an implanted communication module 317'. Optionally, the controller 343' comprises a processor that receives data from a sensor 332' and/or generates an alert (e.g., audio-visual signal transmitted by an indicator 316' and/or an alert transmitted to an external device). Alternatively or additionally, data processing and/or alerts may be performed by processor of the external controller 343'. The controller 343' may optionally read the implant ID number. Optionally, the controller includes onboard management routine, a non-volatile memory (for example for storing data), a communication link to a remote device 345' and/or an implanted device and/or Wi-Fi connectivity to a network (e.g. the Internet). The controller is optionally 343' battery powered. Optionally, the Controller is programmed to automatically initiate a data dump to according to a schedule and/or pending specific conditions. For example, this may facilitate receiving by a physician of an indication when a dialysis session is performed properly, was out of spec and/or missed altogether.

In some embodiments, communication between controller 343' and a sensor (for example implanted sensor 332') is based on a sensor specific ID number. Optionally, the sensor ID number is associated to a specific patient. The controller 343' is optionally designed to collect data from several patients automatically. For example, each data is assigned to the correct patient, based on association between a sensor ID number and a patient ID.

In some embodiments, some components of the system are kept in "sleep" mode until they are activated. For example, an implanted device may include a switch 334 (for example a reed switch which may be activated by a small external magnet that is optionally placed in the controller 343').

In some embodiments, an active implant includes a rechargeable battery 315'. Optionally the size of battery 315' is dictated by the period between charging periods. The Controller 343' optionally includes a charger that sends energy to an implanted charger 313'. For example, charging technology may include through-skin magnetic induction. For example, battery 315' may be charged by placing the controller/charger 343' over the implanted system 303' for a period.

In some embodiments, an offline application includes a tablet/smartphone app (running on a smartphone and/or a tablet). Optionally the app includes some or all of the following functions 1. Enter/update patient ID and details, implant ID number, build patients database
2. Download data from controller, append database
3. Upload data to controller, i.e. date and time, chip ID number, calibration factors
4. Compile reports for local presentation, i.e. table of session's time and date, graph of flow rates over time, graph of flow rate over a specific session.
5. Connect and/or upload data to a network. Optionally the data is ready to be accessed securely by a patient authorized clinician. Optionally data may be uploaded immediately and/or when the controller is charging and/or when the controller is not in use.
6. Downloaded data from a network for example the Controller may be controlled and/or updated and/or may receive message for display to an operator by an authorized clinician, e.g. the patient's Nephrologist, clinic staff and/or the subject's interventionist.
7. Manipulated data to display important information. For example, trends of changes in blood velocity over time may be displayed. The controller optionally incorporates a notification processor that communicates alerts when velocity is below a pre-set threshold. In some embodiments, the controller communicates an alert ahead of time when based on current and/or past data; the system predicts that a value is anticipated to reach a danger zone. For example, an alert may be triggered when the velocity is expected to reach a predetermined threshold in a pre-set time.

An active implant as described requires a chargeable battery, which size is dictated mostly by the period between charging periods.

In some embodiment, a charging time may range between 1 to 10 minutes and/or between 10 to 30 minutes and/or between 30 minutes to 2 hours and/or from 2 hours to 6 hours. For example, charging may be performed between dialysis sessions. Optionally an implanted processor 314' tracks the charge state of the battery 315' and/or sends a notification to the controller 343' when charging is required.

Optionally the technology will facilitate: integrating data from a variety of sensors at a variety of locations and using a variety of measuring methods; online access to data from implanted sensors 332' and/or external sensors for example allowing remote oversight of the clinical conditions (e.g., needle insertion, blood velocity measurement etc.); use of the collected data to learn about trends that would be difficult to detect otherwise (e.g., a change in optical path that might be correlated to vessel's wall thickness and/or to fistula maturation, change in blood velocity).

Figure 4:
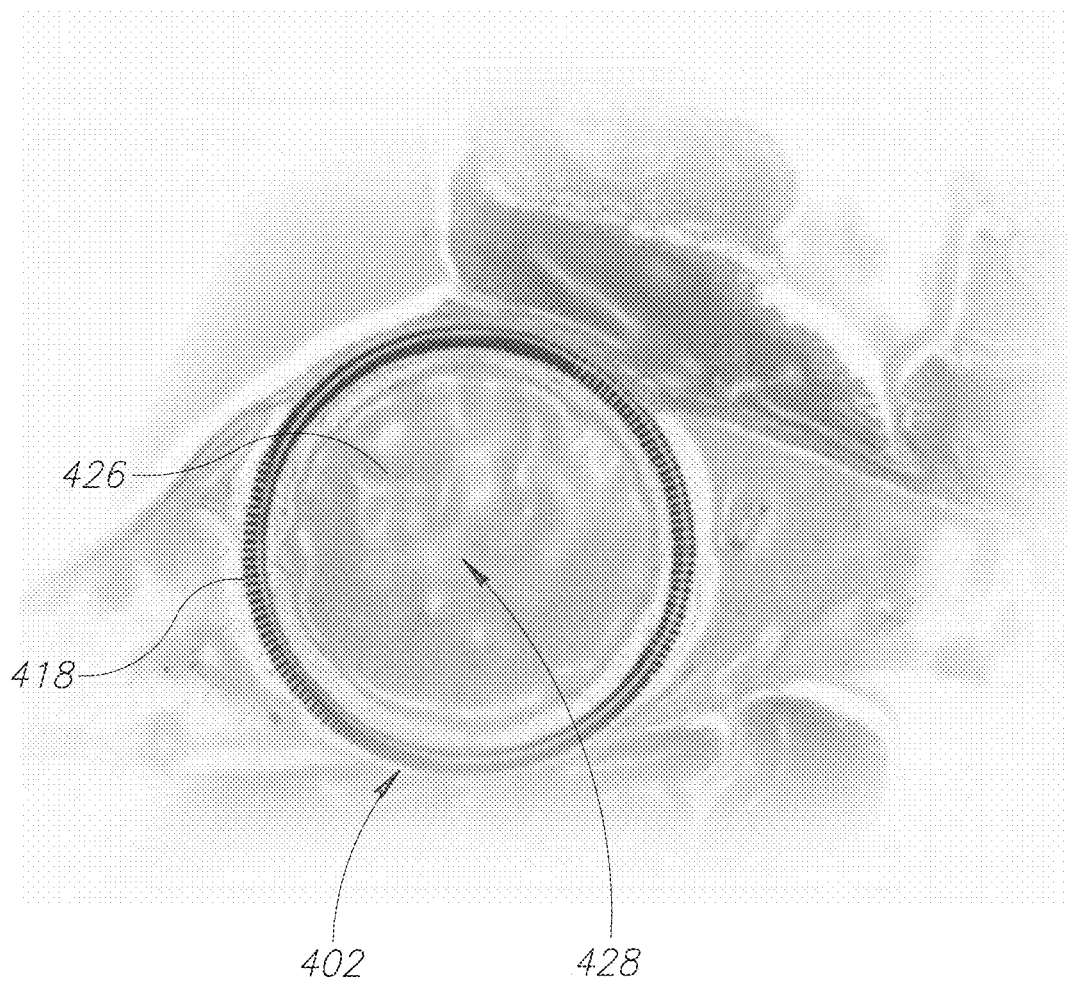
FIG. 4 is a micrograph illustrating growth of tissue in a VAD in accordance with some embodiments of the current invention.

FIG. 4 is a micrograph illustrating growth of vascular endothelial tissue 426 an in a VAD in accordance with some embodiments of the current invention. In some embodiments, a guide 402 of a VAD includes a channel 428 with perforated 418 in its walls. Optionally perforations 418 are configured to enhance growth of a preferred tissue type in the channel 428. For example, perforations of width ranging between 20 μm to 40 μm and or between 40 to 80 μm and/or between 80 to 120 μm have been found to enhance growth of vascularized tissue. In some embodiments, vascularized tissue in a channel may assist in fighting off infection and/or preventing back bleeding. For example, vascularized tissue may wrap itself around the lumen of the device, reducing exposure of bare metal to the needle.

Figure 5:
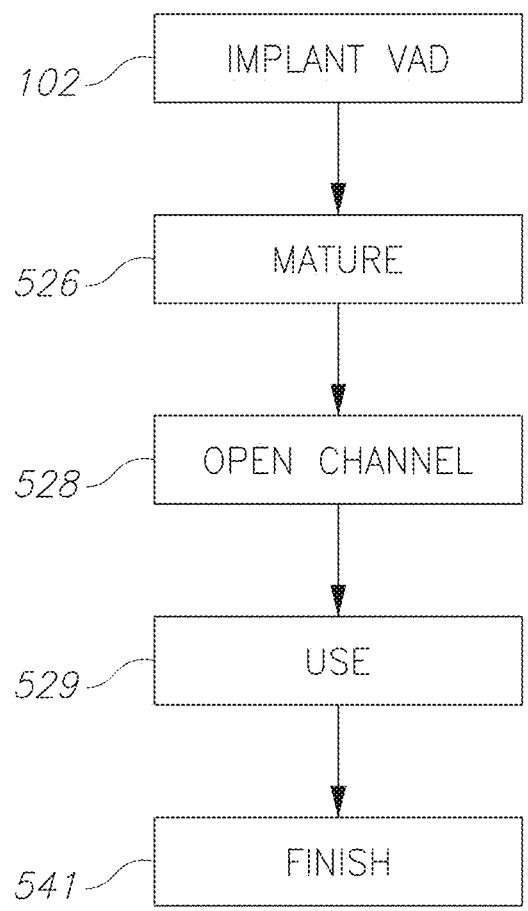
FIG. 5 is a flowchart illustration of a method of providing access to a blood vessel in accordance with an embodiment of the current invention.

FIG. 5 is a flowchart illustration of a method of providing access to a blood vessel in accordance with an embodiment of the current invention. In some embodiments, a VAD is implanted 102 into a subject from the skin to an outer wall of a blood vessel. The VAD is allowed to mature 526. For example, maturing may include growth of endothelial tissue inside a lumen of the VAD.

For example, the VAD may be configured to enhance grow of vascularized tissue within the lumen and/or along the walls of the VAD and/or its lumen. In some cases, vascularized tissue may be composed of a fine network of fibrils. For example, fibrils may extend from spindle shaped nuclei. The network optionally surrounds multiple cavities. For example, the cavities may be filled with blood.

Analysis of the histopathological data in rats is suggests that there may be a time-related increase in the penetration of mesenchymal (connective) tissues within the lumen of the device—the scar tissue, which may block the lumen from needle penetration. Proper sizing of holes in the walls of the lumen may inhibit this growth. For example, in rats, it was observed that in cases with 100 and 200-micron holes in the implant wall at the 4-weeks time point, the relative ratio between the cavernous (i.e. cavities) spaces and the surrounding mesenchymal tissue was relatively low. At 8 weeks, there was an apparent progressive reduction in the "cavernous" component. In the samples that had 60-micron holes in the implant walls, vascularized tissue captured most of the lumen even after 12 weeks of implantation. For example, a VAD may include 60-micron holes (for example holes ranging between 40 to 80 microns). Such walls may inhibit penetration of scar tissue into the lumen.

Optionally, once the VAD is mature a channel is opening 528 from outside the skin to a lumen of the blood vessel, for example by pushing a needle through the skin and/or into a guide of the VAD and/or through the guide to the out wall of the vessel and/or through the wall of the vessel into the lumen of the vessel. Optionally the needle may include a cannulated hypodermic needle and/or an introducer needle and/or an introducer needle and/or a cannula (for example a plastic dialysis cannula) and/or a blunt dialysis needle. The channel is optionally used 529 for blood flow between the blood vessel and a treatment device, for example a dialysis machine. After a treatment, the session may be finished 541 for example by closing up the channel. In some embodiments, finishing 541 includes a procedure to avoid back flow of blood.

Figure 6A:
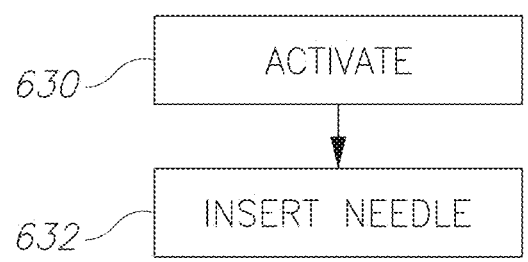
FIG. 6A is a flowchart illustration of a method of accessing a blood vessel in accordance with an embodiment of the current invention.

FIG. 6A is a flowchart illustration of a method of accessing a blood vessel in accordance with an embodiment of the current invention. In some embodiments, a VAD may include active component, for example a sensor and/or an indicator. Optionally before starting a vascular access treatment, the active component is activated 630. For example, activation 630 may be by exposing a switch to an activation signal (for example exposing a reed switch to a magnetic signal). Alternatively or additionally, activation 630 may be by exposing the device to a physical stress (for example tapping the device and/or skin near the device to set off a vibration sensor). Optionally when the device is activated 630 an indicator may be activated indicating a location of needle insertion. Optionally when the needle is inserted 632 to a predetermined position (e.g. when the needle tip reaches the wall of the blood vessel) the indicator is turned off or changed. Alternatively or additionally active components of a VAD may remain active and/or not require activation 630. Alternatively or additionally a VAD may contain only passive components.

Figure 6B:
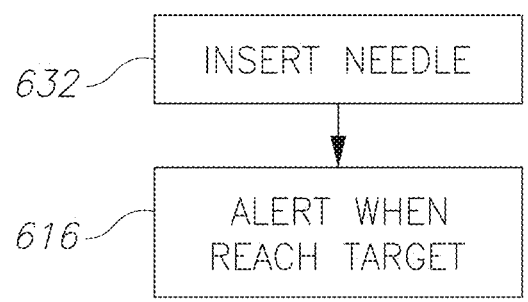
FIG. 6B is a flowchart illustration of a method of opening a channel in an access device in accordance with an embodiment of the current invention.

FIG. 6B is a flowchart illustration of a method of opening a channel in an access device in accordance with an embodiment of the current invention. In some embodiments, a VAD system includes an indicator of needle position. For example, a change in the indicator alerts 616 the operator that the needle is in the critical area, for example near the vessel wall and/or when insertion 632 should be finished. For example, when the device is activated 630, a sensor may be activated. When the needle tip reaches the critical location, the sensor may signal to an indicator to alert 616 an operator. Optionally the indicator may be part of the VAD. Alternatively or additionally, the indicator may be on a separate implanted object. Alternatively or additionally, the indicator may be on a remote object (for example a cell phone that is activated by a wireless signal).

Figure 6C:
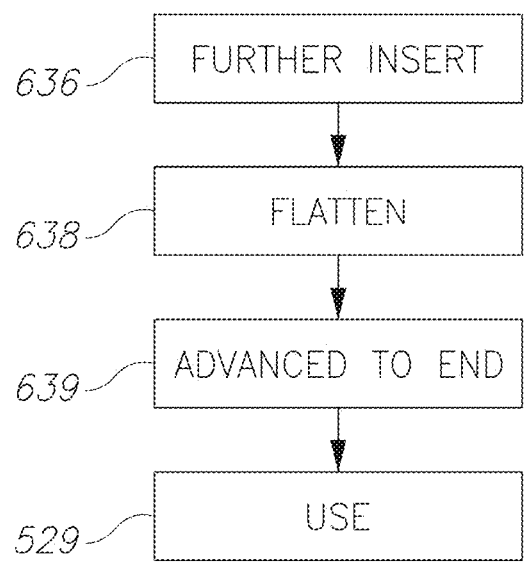
FIG. 6C is a flowchart illustration of a method of opening a channel in an access device in accordance with an embodiment of the current invention.

FIG. 6C is a flowchart illustration of a method of opening a channel in an access device in accordance with an embodiment of the current invention.

Figure 9A:
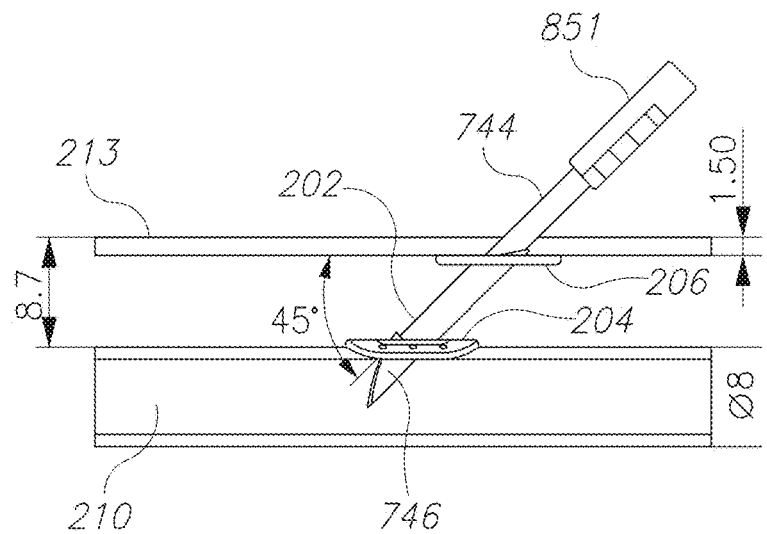
FIGS. 9A-9C are schematic illustrations of flattening a needle in accordance with an embodiment of the current invention.

In some embodiments, the needle is inserted 632 (for example as described with regards to FIG. 6B) into the subject along a guide of the VAD (for example though a guide channel). Optionally, insertion 632 continues until an alert is conveyed 616 to the operator (for example the alert may include an audio signal and/or a visual signal). For example, a needle-locating sensor on the vessel interface of the VAD and/or on a distal portion of the guide will sense when the sharp-needle's bevel is within a critical area (for example when the bevel is near the vessel wall and/or enters the lumen of the vessel for example as illustrated in FIG. 9A). Optionally the sensor triggers an indicator to convey 616 the alert when the needle tip reaches the critical area.

Figure 9B:
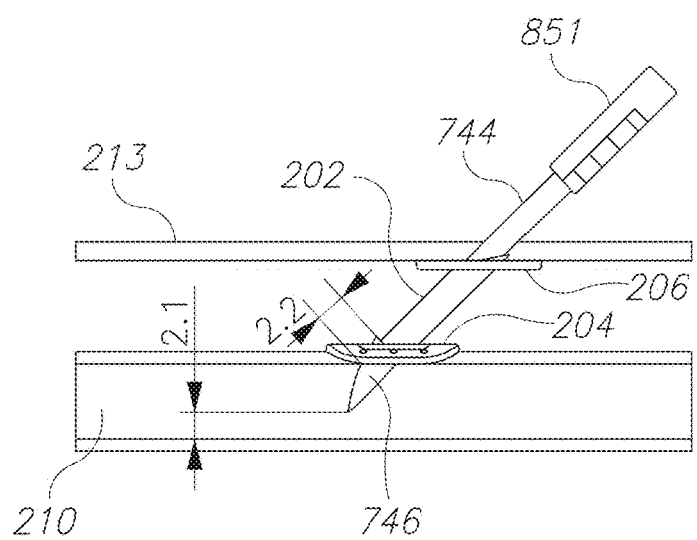

In some embodiments, after the needle reaches the critical area, the needle is further advanced 636. For example, further advance of the needle may range between 0.5 to 1.2 mm and/or between 1.2 to 2 mm and/or between 2 to 5 mm and/or more (for example as illustrated in FIG. 9B). Optionally after advancing 636 the operator aspirates blood into the needle to check if the tip is properly in the vessel. Alternatively or additionally, for example in the case of a plastic dialysis needle with an introducer there may be no aspiration and/or aspiration may follow removal of the introducer. In some embodiments, advancing 636 pushes enough of the needle into the vessel to support the needle from sliding outside the vessel when the needle is flattened 638.

Figure 9C:
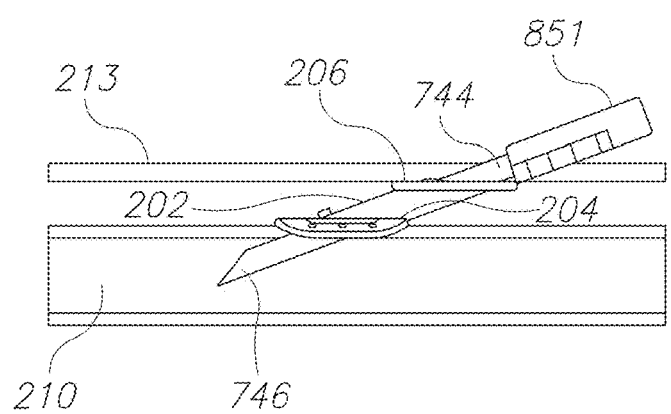

In some embodiments, a portion of the needle assembly that is protruding outside the skin is flattened 638 to the skin. After flattening, the needle is optionally further advanced 639 up till the hub (for example as illustrated in FIG. 9C). In some embodiments, the procedure includes safeguards to avoid perforation of the back-wall of the vessel. For example, by sensing when a needle tip reaches a critical zone near the vessel wall and/or stopping insertion, back-wall perforation is inhibited.

In some embodiments, a needle may not be flattened. For example, a jig may be supplied that supports the needle without flattening the needle against the skin. Optionally, the needle may be inserted precisely into the vessel without further advancing. For example, the length of the VAD and/or the needle may be precisely matched such that the needle reaches the lumen of the vessel but does not reach the back wall. For example, the tip of the needle may be inserted between 1 mm to 2 mm past the front wall of the vessel and/or between 2 to 4 mm and/or between 4 to 6 mm and/or between 6 to 9 mm. Alternatively and/or additionally insertion may be at a low angle (for example less than 30 degrees and/or less than 20 degrees and/or less than 10 degrees). For example, low angle insertion may reduce the probably of puncturing the rear wall of a vessel and/or may allow a large degree of insertion without flattening. In some embodiments a jig may be used to control the angle of insertion and/or length of insertion and/or to stabilize the needle without flattening.

Figure 6D:
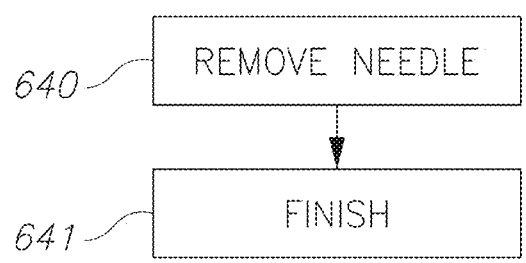
FIG. 6D is a flowchart illustration of a method of closing an access device in accordance with an embodiment of the current invention.

FIG. 6D is a flowchart illustration of a method of finishing 641 use of an access device in accordance with an embodiment of the current invention. In some embodiments, finishing 641 includes closing a channel and/or inhibiting back bleeding. For example, the channel may close by itself when a needle is removed 640 due to the elasticity of the vascular tissue in the VAD lumen. Alternatively or additionally, external pressure may be applied to close the VAD lumen and/or prevent back bleeding. For example, the pressure may be created by an operator putting pressure on a chosen location on the skin near the VAD. For example, the VAD may be configured to facilitate an operator putting pressure on the right location to close up the vessel wall and/or stop back bleeding. Optionally an indicator is provided showing where and for how long to apply pressure. For example, when a sensor detects that a needle has been removed, an indicator may be lit up at indicating the pressure location. Optionally the indicator will remain lit (for example for a predetermined time period and/or based on a sensed condition) until it is safe to remove pressure. Alternatively, a VAD may passively indicate a pressure location (for example the location may be a fixed distance on a particular side of the VAD. Alternatively or additionally, the VAD may be designed for self-closing. For example, the VAD guide may include a thin elastic lumen that expands when a cannula is pushed through the guide and/or elastically closes (and/or squeezes closed the vascular tissue in the VAD) when the needle is removed. Alternatively or additionally, back bleeding may be prevented by inserting an obturator into the VAD before, during and/or after needle retraction.

In some embodiments a dialysis needle that was introduced through the VAD into the vessel (for example a fistula) will be withdrawn a designated distance (for example between 5 to 15 mm) from the vessel. For example, the needle tip may be positioned within between 1 to 10 mm from the end of the VAD at its connection to the vessel. Optionally the lumen of the dialysis needle may then be occluded with a blunt obturator passed down a lumen of the needle. Optionally the obturator is left in place for a time ranging for example from 30 second to 10 minutes. Optionally this will cause stasis of blood in the distal 5-15 mm of the VAD with that stasis resulting in the formation of a small blood clot plug. This optionally prevents back bleeding into the remaining channel of the VAD In some embodiments, the cannula that traverses the VAD and enters the blood vessel may include a balloon at its distal tip. At the end of dialysis, the balloon is positioned between 1 to 15 mm from the distal end of the VAD, and the balloon is inflated (for example from a port on the plastic cannula that is protruding from the skin). The balloon will remain inflated for a time ranging for example between 30 seconds and 15 minutes and then deflated. This may facilitate formation of clot or plug that will prevent back bleeding into the lumen of the VAD.

Figure 7A:
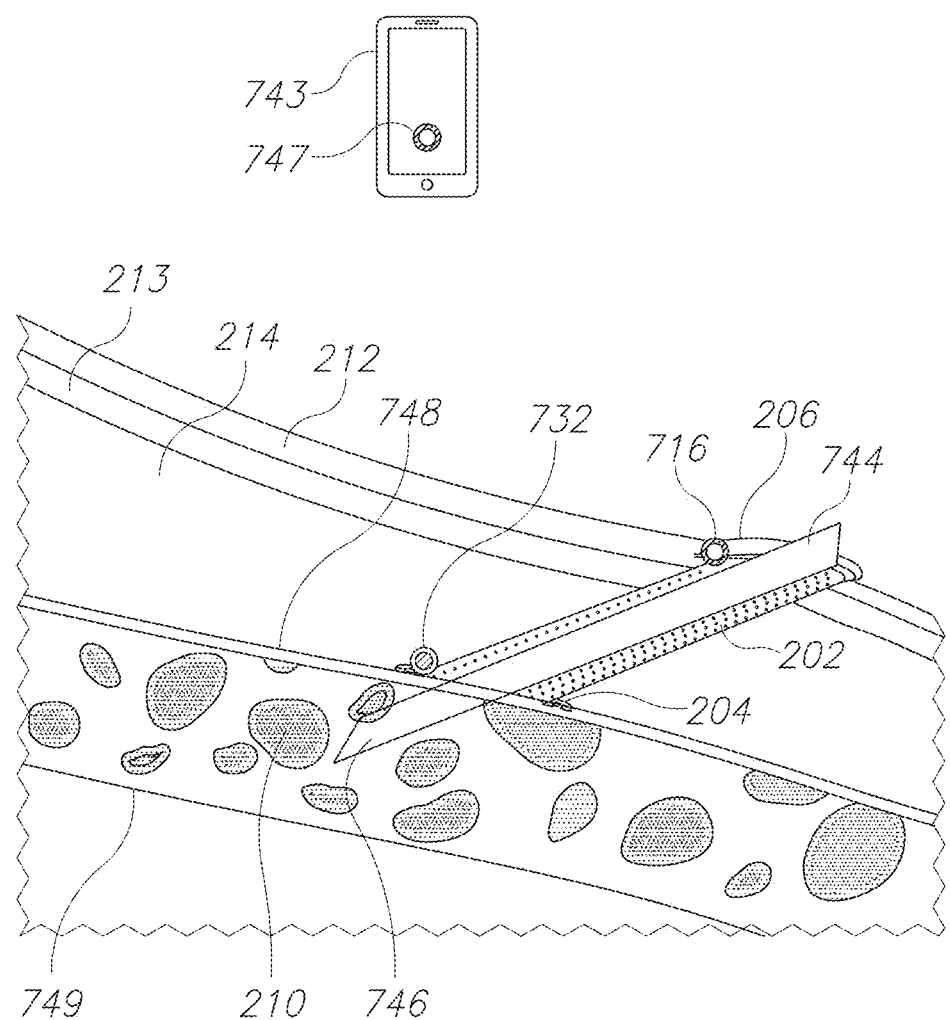
FIG. 7A is a schematic illustration of a vascular access device with a sensor and/or an indicator in accordance with an embodiment of the current invention.

FIG. 7A is a schematic illustration of a vascular access system with a sensor 732 and/or an indicator 716 in accordance with an embodiment of the current invention;

In some embodiments, in hemodialysis treatment, blood is circulated through two needles that access a blood vessel from the outer skin. Optionally, outside the subject, the needles connect to plastic tubes vessels that circulate the subject's blood across a dialysis membrane. Optionally, a VAD is supplied for each needle. In some embodiments a sensor is used to track the location of each needle tips. Knowing the position of the needle tips may facilitate a needle tip penetrating a blood vessel's front wall and remaining within the lumen without being advanced too far and/or perforating the blood vessel's back wall. In the ordinary medical practice, detection of needle location may be done manually by a clinician who takes specific actions to determine the needle tip's place.

Some embodiments of the present invention relate to a system and method to detect the tip of a cannulating device that is inserted through the skin on a path to penetrate a blood vessel wall. As described in exemplary embodiments below, the system may include an implant that incorporates sensing and data gathering components. Optionally data collected from the sensors during the treatment and/or during at other times are used monitor the care and/or condition of a blood vessel.

The embodiments described below are applicable to a variety of interventions and a variety of tools. In a narrow view, they are applicable to a needle guide apparatus as will be described below. More broadly, they might be applicable, in whole or in part, to any vascular access device. In a much broader view, implanted sensors and data management tools may promote care in other implant and/or interventional tools that are used in a variety of medical areas for example implanted joints (hip or knee, etc.) or grafts.

By the way of illustration, a single needle 744 accessing a blood vessel 210 through a VAD is illustrated in FIG. 7A. For example, in a hemodialysis session, another needle and/or VAD may be supplied elsewhere in vessel 210 for recirculating the blood passing through needle 744. The embodiment of the invention illustrated through its application for one needle insertion during hemodialysis as presented for example below, may be used in other applications.

Detection of location of a needle tip 746 in hemodialysis may be safety feature that helps indicate when a needle is adjacent to the vessel front wall 748 and/or to help prevent AVF back-wall 749 perforation. When a dialysis needle is advanced by the operator to the vessel 210 more than required, it may puncture the back wall 749 of the vessel (and/or graft). It has been postulated that back-wall perforation is a significant contributor to fistulae failure.

An implanted device can be designed to guide a needle 744 to enter the vessel 210 in a predetermined location, orientation and distance. Optionally, needle guide 202 of a VAD includes a cylindrical conduit having a diameter ranging between 1 to 4 mm and/or between 4 to 6 mm and/or between 6 to 10 mm. The VAD is optionally placed by a surgeon from under the skin to the outer wall of the vessel. In some embodiments a VAD for implantation in an upper arm may have a length ranging from 5-25 mm. and it may have a skin interface 206 and/or vessel interface 204 that enable suturing the VAD to the dermis 213 and/or to the front wall 748 of blood vessel 210.

Some embodiments of a VAD system include a needle detecting sensor 732. Sensor 732 optionally sends an alert when the tip 746 needle 744 (and/or another tool) is entering a "risky" zone, i.e. approaching or puncturing the front wall 748 of a vessel 210. For example, when needle tip 746 enters the critical zone, sensor 732 will trigger an indicator 716 to alert an operator. For example, the operator will stop advancing the needle 744 before it hits the back wall 749. Alternatively or additionally, sensor 716 may trigger transmission of a signal to an external device and/or a network device 743 which may alert the operator. For example, a signal is transmitted to a cellular device which may give over a visual and/or audio alert 747. In some embodiments, an alert is sent every time that needle is detected to enter the "risky" zone. For example, an operator may advance and withdraw the needle according to the clinical needs and be alerted whenever the needle is approaching the "risky" zone.

In some embodiments, detection is made through a sensor 732 that is encapsulated in a distal end of an implant adjacent to the vessel 210 being accessed. For example sensor 732 may include a magnetic sensor that detects a change in a magnetic field due to the proximity of needle 744. Alternatively or additionally, sensor 732 may include optical or electric field sensing technologies. Optionally sensor 732 has dimensions of less than 1 mm. For example, detector 732 detects a metal component (for example needle 744) when it enters the lumen at the distal end of the guide 202.

Sensing technologies that may be used an embodiment of the current invention include for example:

In some embodiments, an optical sensor may detect when an object breaks a light path between a light source and a light detector. For example, the sensor may sense when the needle tip breaks a light path from a light source to a light detector (for example the light source may include a LED and/or the detector may include a photodiode). Source and detector are optionally mounted so that the needle enters between them and breaks the light path. Light may be at any wavelength for example in the IR to UV range. The location of the source and detector is designed to have the needle break the light path when the tip reaches the critical zone.

In some embodiments, an optical sensor may detect when an object reflects light path from a light source to a light detector. Source and detector are optionally mounted on the same side of the guide so that the needle reflects light back from the sensor to the detector. Light may be at any wavelength for example in the IR to UV range. The location of the source and detector is optionally configured to have the needle reflect the light when the tip reaches the critical penetration depth.

In some embodiments, an optical sensor detects when the needle disperses light from a source so that at least some is diverted towards a detector. Source and detector are optionally mounted at an angle of their optical axes which is different than either 180 ((case a) or 0 (case b). For example, the angle may range between 0 to 15 degrees and/or between 15 to 45 degrees and/or between 45 to 75 degrees and/or between 75 to 90 degrees. The location of the source and detector is optionally configured to have the needle disperse at least part of the light towards the sensor when the tip reaches the critical penetration depth.

Optional a light may be guided to the desired location from a light source and/or to a detector using an optical fiber. For example, one end of the fiber may be positioned as described for the source and/or detector described above and/or the other ends may be connected to an internal and/or an external light source and/or detector. For example, the second end of the optical fibers may be implanted in the subcutaneous layer with the open ends facing outward, at two different locations. For example, a laser may be used to light one of the fibers and/or transmit light through the fiber. Part of the light is optionally received by the other fiber and or sensed by an external optical sensor. For example, the detector and/or light source may be on an external controller. For example, when the needle enters the space between the fibers, the intensity of the received light changes and/or indicates the location of the needle.

In some embodiments, a sensor includes a magnetic field detector (for example a Hall Effect detector or other). Optionally the system includes an adjacent electromagnet or permanent magnet. Alternatively or additionally, the system may not include an adjacent electromagnet or permanent magnet. Some objects, for example a metal needle and/or introducer needle may create a change in magnetic flux near the detector as it comes close. For example, the change may increase in magnetic field if needle is ferromagnetic, and/or a decrease in magnetic field if needle is diamagnetic. In some embodiments the system may not be sensitive to non-magnetic materials (i.e. a plastic cannula).

In some embodiments, a sensor includes an eddy current detector, for example using a coil driven by a high frequency current (for example in the 100 KHz-100 MHz range). Approaching conductive needle may increases losses due to eddy current induced in the needle. The location of the coil is optionally such that the losses trigger the sensor when the tip reaches the critical penetration depth.

In some embodiments, a sensor includes s mechanical switch. For example, the switch may be pressed and/or released by mechanical pressure from the needle as the tip reaches the critical penetration depth.

In some embodiments, a sensor includes a strain gauge (for example resistive, piezo and/or optical). For example, the gauge is installed at the correct depth and/or coupled to a lumen of a guide. The gauge optionally detects a deformation of the tissue or a blood clot filling the lumen of the guide as the needle enters and/or displaces the lumen wall.

In some embodiments, a sensor includes an electrical conductivity detector. For example, the detector may detect a change in electrical conductivity perpendicular through the lumen of the guide, between two electrodes in DC and/or AC currents. Optionally, current is passed through a cross-section of the lumen of the guide at the desired penetration depth. For example, current may be increased for a conductive needle and/or decreased for an insulating needle, as the needle is inserted between the electrodes.

In some embodiments, a sensor includes a capacitive proximity detector. For example, the detector may detect a change in the electrical capacitance between two electrodes positioned in and/or near the lumen at the desired penetration depth, or between a single electrode positioned at the desired penetration depth and the body of the guide for example for a guide made from a conductive material. The capacitive detector optionally makes use of a conducive electrode which is electrically insulated from the body but is capacitively coupled to the lumen of the guide.

In some embodiments, a sensor includes an electric field strength detector. For example, the detector may monitor strength of a high-frequency RF field which changes as a conductive needle approaches the detector. For example, the sensor may be configured to detect when the tip reaches a critical penetration depth. For example, the detector may be implemented as an RFID chip. Optionally the chip is mounted on the guide and/or powered by an RFID reader outside the body. Communications may include a series of "interrogate and response" cycles. For example, the chip may be shielded and lose communication as needle approaches.

In some embodiments, the field may be adjusted to increase beyond a predetermined receiver threshold so that a response from the RFID chip will be received as soon as the needle tip approaches the critical zone. Optionally the entire RFID chip less just 0.5×0.5 mm. The small size of the chip optionally facilitates spatial resolution on a scale similar to the size of the chip for example of between 0.1 to 0.4 mm and/or between 0.4 to 0.7 mm and/or between 0.7 to 1.0 mm. A RFID chip is optionally embedded in a suitable hole in the guide and/or vessel interface of the VAD. For example, the detector may be mounted close to the needle path. The position of the detector may be configured to increase the effect of the implant metal. In some embodiments, use of an RFID tag detector may facility positive identification of the patient by the controller and/or relatively simple implementation.

In some embodiments, a sensor includes an ultrasonic proximity detector. For example, the detector may measure time of flight of ultrasonic pulses, and/or activation the detection signal as the needle tip reaches the critical penetration depth. This type of sensor may optionally be adjusted to different penetration depth by remotely programming the sensors electronics. Alternatively or additionally a sensor may include a one or a few piezo detectors whose resonance frequency and/or electro-acoustic impedance changes as the needle comes in close proximity or contact with the detector.

In some embodiments, a miniature coil is attached in proximity to an RFID tag. Optionally the coil is connected through flexible leads to a larger coil implanted under the skin at the target position. For example, an external controller may be positioned to activate the larger coil. The inductance of the implanted coil optionally changes abruptly when the needle enters the area under its cross-section, and this change may be read through the subcutaneous coil and a matching circuit in the controller. Alternatively or additionally, detection of a change in a magnetic field may be detected when a metal piece (e.g. the needle) enters a cross-section of a coil. For example, an electrically powered coil may be positioned to surround a needle path of a guide. For example, the coil may be positioned adjacent to the vessel wall and/or generate an electrical current when a metal needle enters the cross section.

Some optional potential advantages of including active elements in an implant include that the active elements may facilitate:

a. tracking stock by item number without opening the case;
b. recognizing of a particular implant and/or patient;
c. collecting data from several patients with a single controller and/or automatically assigning each data to the correct patient and/or assigning a serial number to a patient's ID.

In some embodiments, a sensor includes an ultrasonic wave emitter and/or detector. For example, the sensor may be installed on the VAD close to the vessel to measure blood flow inside the vessel. This type of sensor may optionally be adjusted to different diameters of the vessel by remotely programing the sensors electronics.

In some embodiments, a controller is programmed to automatically initiate a data dump according to a schedule or pending specific conditions. For example, the data may be stored in a computer readable memory accessible over a network. For example, this may facilitate updating a subject and/or clinician. For example, an alert may be generated when a dialysis session was out of spec and/or missed altogether. Optionally, data collected and transferred may comply with HIPAA regulations in the US, or similar regulation in other countries.

In some embodiments, the system may operate in multiple modes. When certain components are not present the guide may be used as in a passive mode. When some active components are present, the system may facilitate measurement of vessel patency only. When more active components are present, the system may open up a larger range of functions.

In some embodiments, recognition of a subject and/or individualized data communication between an implant and the dialysis machine may facilitate setup of procedure parameters based on the unique ID of the implant and/or patient. Such customized setup may be automated.

When a needle is detected, the sensor optionally sends a signal through the one or more of following methods:

In some embodiments, a light source (e.g. narrow beam LED) that is encapsulated in the VAD (for example in the proximal (skin) side thereof) is switched on by the sensor. Optionally the light of the LED is observable near the insertion point of the needle and/or is observable by the operator who is inserting the needle. The light type and intensity may be configured to be observable on different skin colors and under different ambient lighting conditions.

In some embodiments, an alert is transmitted wirelessly. For example, a Bluetooth Low Energy (LE) communication sends a sensor signal to an external device. For example, the external device may include a dedicated device (for example a controller, as described in various embodiments herein) and/or to a generic wireless enabled device (for example a tablet/smartphone, etc.) running the device's application. The external device optionally activates an audio and/or visual alert.

In some embodiments, use of a needle sensor may facilitate use of a plastic dialysis cannula. One problem identified in the adoption of plastic cannulas is that some operators are trained to recognizing penetration of a blood vessel by flashback through a hollow needle. The introducer needle inside the cannula may make recognition of such flashback difficult. In some embodiments, use of a needle sensor may facilitate recognition of penetration of a blood vessel by the introducer needle.

In some embodiments, needle may be used having different size, shape and/or material. Different detectors may be used for different needles.

In some embodiments, a needle locator alarm may comprise a needle detector, a control circuit, an activation device, an indicator device and/or a power source. The system may include a through-the-skin charging device. Optionally, components of the locator are implanted as part of the needle guide of a VAD. Alternatively or additionally the needle locator may be installed separately as an add on device. For example, some parts may be attached to VAD and/or other parts may be implanted in a separate compartment and/or connected to the guide-attached parts for example with a cable. Alternatively or additionally, the needle locator may be a totally-separate unit from the VAD and/or may be implanted in close proximity to the VAD.

In some embodiments, a needle detector system may comprise one or more separate needle guides, and the control algorithm may provide different indications based on temporal relationships of needles insertion and removal from the different guides. Optionally the needle detector system may include a blood flow sensor for example for applications involving blood flow through the needle.

A memory module in the implant may store some and/or all the information generated by the various sensors. Optionally the data will be stored with a real time stamp. Optionally the data is retrieved at a later time as a means to review the cannulation process. Data items collected may include for example:

A. Time first needle was inserted,

B. Time second needle was inserted until all the needles are in place

C. Time flow activated

D. Time when flow was stopped

E. Time first needle was removed,

F. Time second needle was removed until all the needles are in removed

G. Any alarms generated during the process, such as a needle removed while flow is ON, or a too long period between insertions or removals of the various needles.

H. Communication with the module may be implemented using a wireless link, for example the same link used for receiving the alarms to the external device.

I. Battery status at any time

J. Time and duration of charging cycles.

K. Blood flow through needle

The components of the locator are as described below.

Figure 7B:
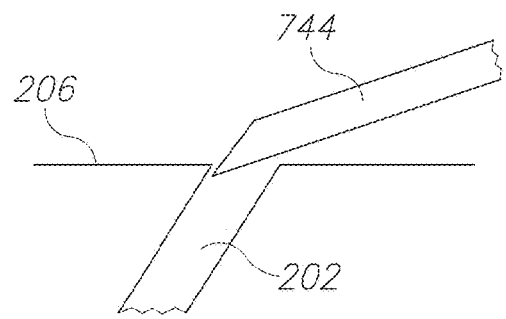
FIG. 7B is a schematic illustration of insertion of a needle at too low an angle into a vascular access device in accordance with an embodiment of the current invention.
Figure 7C:
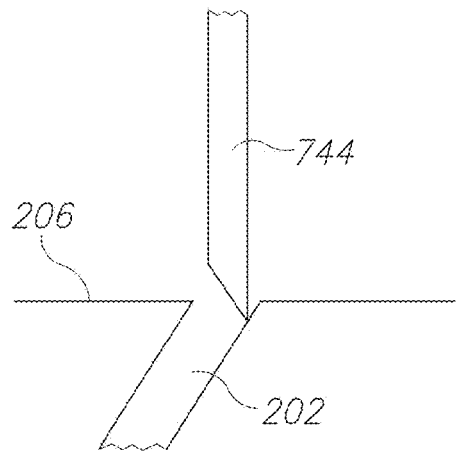
FIG. 7C is a schematic illustration of insertion of a needle at too high an angle into a vascular access device in accordance with an embodiment of the current invention.

FIGS. 7A and 7B are schematic illustrations of insertion of a needle at too low and too high angles respectively into a vascular access device in accordance with an embodiment of the current invention. In some embodiments, a proximal portion of the lumen 220 may be reinforced to prevent puncturing when a needle is inserted at the wrong angle (for example at too high an angle and/or too low an angle). Optionally, the needle 744 may slide downward into the lumen 202 when inserted at a high or low angle. Optionally, the proximal opening of the lumen 202 may be shaped to encourage the needle to slip to the preferred angle, for example the opening may be beveled. In some embodiments a close fit between the lumen 202 and the needle 744 may reduce the possibility of insertion at a non-preferred angle. For example, the needle may enter less than 1 mm and/or between 1 to 2 mm when the angle directed at an angle differing from the guide by more than 5 degrees and/or more than 10 degrees and/or more than 20 degrees.

Figure 7D:
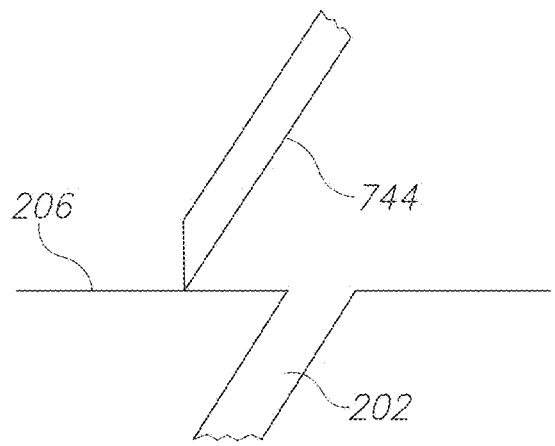
FIG. 7D is a schematic illustration of insertion of a needle ahead of a vascular access device in accordance with an embodiment of the current invention.
Figure 7E:
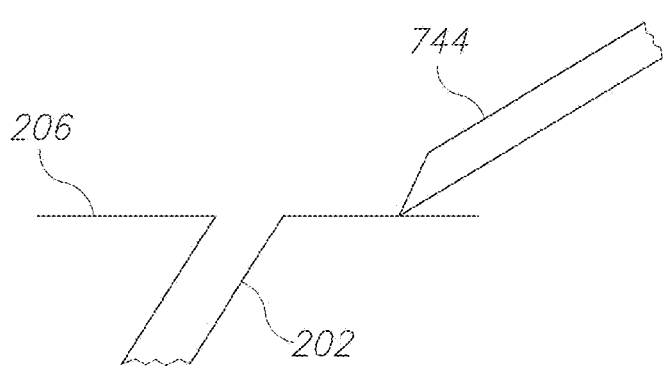
FIG. 7E is a schematic illustration of insertion of a needle behind a vascular access device in accordance with an embodiment of the current invention.

FIG. 7D is a schematic illustration of insertion of a needle ahead of a vascular access device in accordance with an embodiment of the current invention. FIG. 7E is a schematic illustration of insertion of a needle behind a vascular access device in accordance with an embodiment of the current invention; In some embodiments, the skin interface 206 is configured to inhibit insertion of a needle through the skin in the vicinity of the VAD lumen 202 but not through the lumen. This may protect tissue around the VAD from disruption and/or protect the guide of the VAD from external puncture. This may help protect the blood vessel in the vicinity of the VAD from external puncture. In some embodiments, the skin interface 206 may be tilted toward the lumen 202 for example to encourage the needle to slide into the lumen 202.

Figure 8:
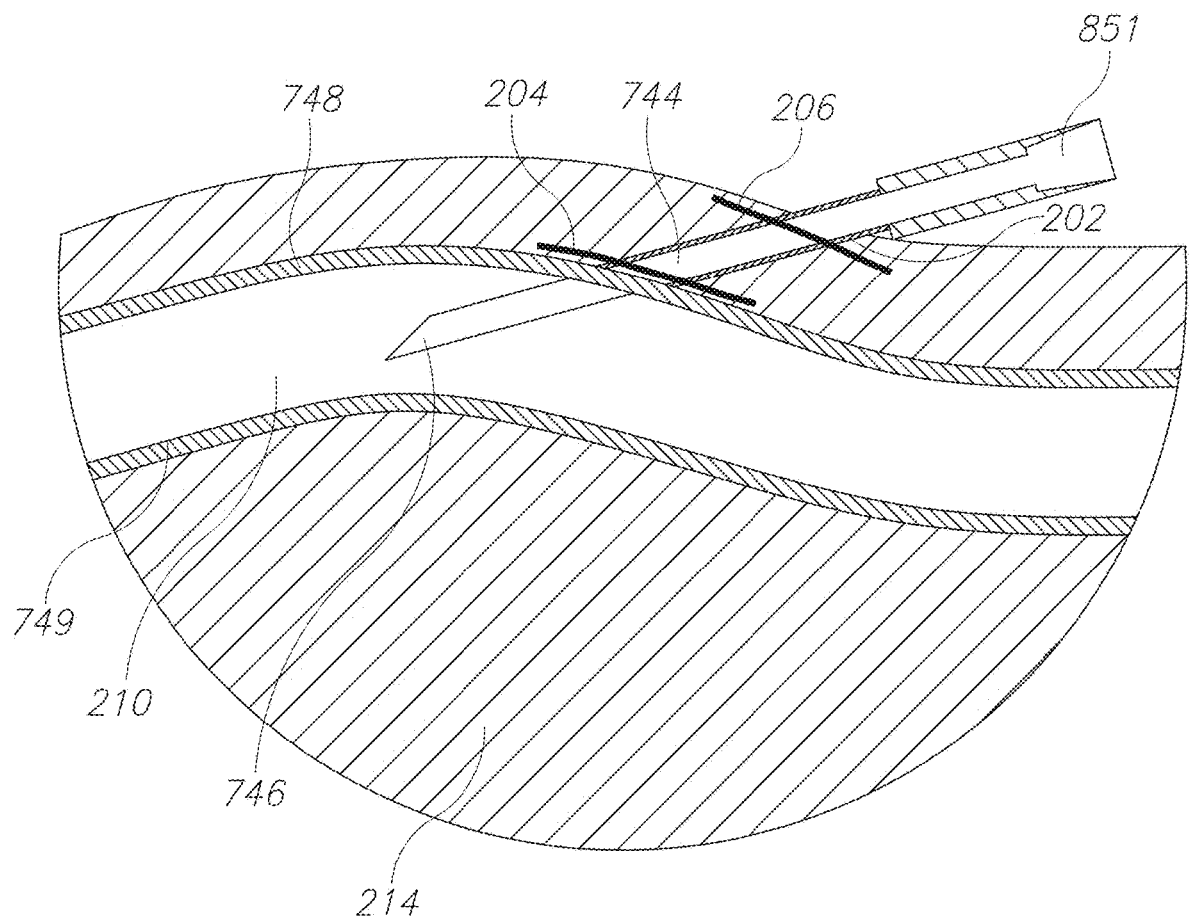
FIG. 8 is a schematic illustration of flattening a needle in accordance with an embodiment of the current invention.

FIG. 8 is a schematic illustration of flattening a needle in accordance with an embodiment of the current invention. In some embodiments, after the needle tip 746 has penetrated the front wall 748 of the vessel 210, an external hub 851 of the needle 210 is flattened against the skin. This may cause the needle tip 746 to approach the inner surface of the front wall 748 of the vessel 210. From a flow dynamic perspective, it may not be desirable for the flow to exit the needle too close to the vessel wall 748. In some embodiments, the vessel interface 204 of the VAD will be configured to cause bending of the vessel (for example by a long rigid footplate) that will keep the needle tip 746 near the center of the blood vessel. However, on the other hand, a long footplate may elevate the front wall 748 and/or distort the vessel shape which in some embodiments may lead to an undesirable change in blood flow dynamics. In some embodiments a VAD may include a shortened foot plate. For example, a footplate may protrude less than 2 mm from the guide. This optionally keeps distortion of the vessel within a desired range. Alternatively or additionally, a flexible joint may connect between the foot plate and the guide of the VAD and/or the vessel interface may be flexible and/or bent at an angle slightly biased toward the angle of the plate when the needle is flattened. Alternatively or additionally, a flexible cannula (for example a plastic dialysis cannula) may be used. For example, a slight lift of the front wall 748 may keep the flow away from wall 748 without distorting vessel 210 too much. In some embodiments, flattening of a flexible cannula may not distort the vessel at all. The cannula is optionally pushed into the vessel and/or changes direction when it enters the vessel. Optionally, the cylinder angle of the VAD with respect to the vessel will be designed to change from high at the skin side (e.g., 30 deg. Or even 45 deg.) to small at the vessel side (e.g., 10 deg.). This change optionally enables an easy entry into the vessel in a way that flow that comes out of the needle is close to parallel to the vessel direction. Flattening will bend the proximal end of the cannula towards the skin without transforming forces to the cylinder.

FIGS. 9A-9C are schematic illustrations of inserting, advancing and flattening a needle in accordance with an embodiment of the current invention.

In embodiments the angle between a guide 202 and the skin and/or is set initially by the surgeon during the implantation according to the patient's anatomy. In some embodiments, a VAD is configured to conform to an angle range between 20 to 45 degrees. In some embodiments a VAD will have a fixed angle and/or there will be a variety of different VAD's of different angles and/or different lengths available to the surgeon. For example, a kit may be sold having an assortment of VAD's of different angles. Alternatively or an additionally, VAD may have an adjustable angle which the surgeon sets before implantation. The angle can further change slightly after implantation to reduce the extent that the vessel is distorted when the needle is levelled to the skin by the nurse. In some embodiments, an implantation kit may contain one or more VADs and/or other components (for example active components and/or boxes).

In some embodiments, a VAD may have customized length and/or an adjustable length. For example, a VAD may telescope and/or a long VAD may be trimmed to a shorter length. Optionally, the VAD may be shortened when attached to a shallow vessel and/or lengthened when attached to a deeper vessel. For example, a VAD may length may be adjustable lengths between 15 to 20 mm and/or between 20 to 35 mm and/or between 35 to 50 mm. Optionally, the VAD will be installed at the same angle to the skin for vessels at different depths. For example, the VAD may be installed for needle insertion at an angle between 15 to 35 degrees.

In some embodiments, during implantation, the surgeon will fit the VAD to the patient's anatomy and the VAD angle. For example, the VAD angle may be adapted to an angle ranging between 20 to 45 degrees, according to the depth of the vessel. For example, for a deep vessel the angle may be steep, e.g. close or even more than 45 degrees. For example, for a shallower vessel the angle may be less. Alternatively or additionally, the surgeon may use the longer VAD for deeper vessels and/or a short VAD for shallow vessels. Optionally a short VAD may be used with a 25 mm needle and/or a long VAD may be used with a 31 mm needle. The same rational may apply for the needles of different composition and/or size (for example plastic needles).

In some embodiments, an angle of a VAD is chosen to allow a VAD of a single length to access vessels at different depths. For example, a 13 mm VAD is optionally installed at an angle of 30 degrees, for example, to reach a vessel at a depth of 6.5 mm. For example, a 13 mm VAD is optionally installed at an angle of 20 degrees; for example, to reach a vessel at a depth of 5.1 mm. For example, a 13 mm VAD is optionally installed at an angle of 45 degrees; for example, to reach a vessel at a depth of 8.7 mm In some embodiments, the sensitivity of the needle tip position sensor will depend on the angle of insertion. Optionally the sensitivity may set according to the angle and/or depth to the VAD.

FIG. 10 is an illustration of a vascular access device with a flexible vessel interface 1004 and/or a flexible skin interface 1006 in accordance with an embodiment of the current invention. For example, the vessel interface 1004 and/or the skin interface 1006 may include a rigid curved plate. Optionally, the plate is connected to a needle guide 202 by a flexible joint.

In some embodiments, the guide may pivot with respect to an interface 1004, 1006 over a range of angles for example between 30 to 40 degrees and/or between 20 to 45 degrees and/or between 10 to 75 degrees. Optionally the flexible joint may include a sliding joint and/or a hinge. In some embodiment, the hinge or joint may be sealed by a flexible covering 1053 (for example silicone) for example the cover 1053 may prevent tissue from growing into the joint. Alternatively or additionally, the joint and/or the plate may be flexible allowing movement of the guide with respect to the attached skin and/or vessel.

In some embodiments, an indicator includes a light pipe 1054 (for example an optical fiber) that illuminates a portion of the VAD. For example, light pipe 1054 is connected to the silicone cover 1053 such that when light is supplied via the light pipe 1054, cover 1053 glows and/or is visible to an operator outside the subject. For example, when the VAD is activated, cover 1053 at the skin side of VAD will illuminate and/or indicate the needle location for needle insertion. Optionally, when the needle point 746 reaches a critical zone, a sensor 1032 will extinguish the light source. Extinguishing the light optionally serves as a notice to the operator that he should stop needle insertion and/or advance only a set distance further and/or proceed with caution. Alternatively or additionally, the indicator may glow in a first color (e.g. green or blue) until the needle tip reaches a critical location and/or another color (e.g. yellow or red) when the needle tip reaches the critical location. Optionally there may be multiple colors, for example green proceed; yellow approaching a critical location—proceed carefully; red reached critical location—stop. Alternatively or additionally, the indicator may remain dark until a critical point has been reached at which it will light up. In some embodiments timing of light may signal needle position. For example the silicon ring may glow constantly when the device is activated and/or blink when the sensor 1032 detects that needle tip is nearing a critical point and/or be extinguished when a critical location has been reached. Alternatively or additionally, the light can change in a way that it presents the operator the preferred direction and/or orientation of the needle in order to enter smoothly through the VAD.

Optionally a plate and/or a joint and/or a guide may be made of titanium and/or Nitinol and/or Stainless Steel (SS e.g. 316L). Additionally or alternatively, the joint may have a flexible cover. For example, link between the guide and the plate may be flexible and/or the cover may protect an area surrounding a sliding joint to prevent tissue growth into the joint. Optionally a joint will be designed and tested for continuous angle change between 20 and 45 degrees. In some embodiments, the torque that bends the joint may be kept small to avoid forces on the vessel that supports the footplate. For example, the joint may be protected from tissue growth that may stiffen it. Optionally the vessel interface and/or skin interface will have a length of between 5 to 20 mm \and/or a cylindrical shape (for example like $\frac{1}{12}$ of a circle). For example, the radius of curvature of the plate may be bigger than the expected radius of curvature of vessel (for example ranging between 3 to 12 mm). Optionally the vessel side interface may have a cylindrical shape and/or the skin interface may be flat and/or circular. Alternatively or additionally, the skin interface may have a shape of a half-dome. Optionally the edges will be deeper in the skin. The deep edges optionally prevent skin erosion near the skin edges. The deep edges optionally improve perfusion to the skin that is above the plate and/or prevent necrosis. The design details optionally depend on the material of the joint—for example SS, Titanium and/or Nitinol. Optionally a flexible cover may have a shield to protect it from damage if a needle miss guide.

Figure 11A:
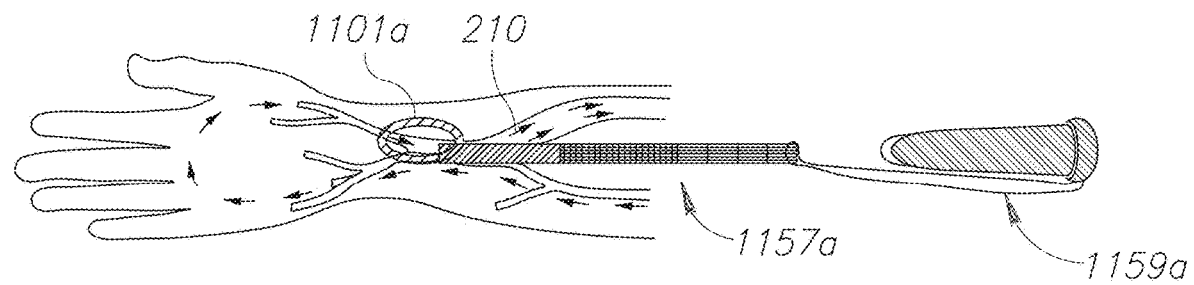
FIGS. 11A and 11B are schematic illustrations measuring blood velocity in accordance with an embodiment of the current invention.
Figure 11B:
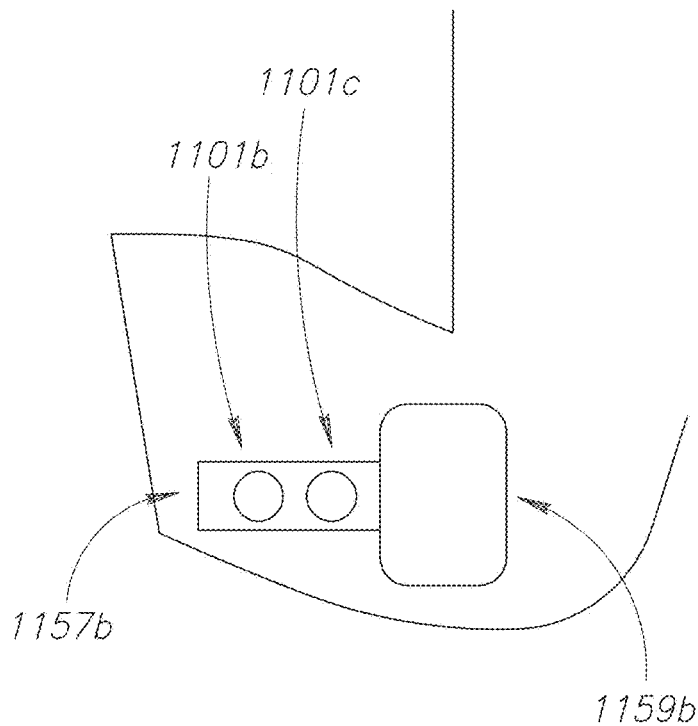

FIGS. 11A and 11B are schematic illustrations of a system for measuring vascular parameters in accordance with an embodiment of the current invention. In some embodiments, a measurement system takes advantage the fixed positions of one or more VAD to position sensors 1032 at a fixed location relative to a blood vessel. For example, the same positions may be used to measure a parameter over a long time period and/or to analyze changes in the vessel. Optionally a sensor and/or an actuator may be fixed to the VAD. Alternatively or additionally, a fixed position VAD may be used as a marker to position a movable sensor. For example, the sensor may be used to measure properties of a fistula and or hemodynamics. In some embodiments, an external sensor 1159a positioned with reference to a VAD 1101a. In some embodiments, a VAD 1101a is permanently attached to a specific location on a blood vessel 210 and/or is used as a marker for aiming (e.g. positioning and/or orienting) an external sensor 1159a. For example, the external sensor 1159a is positioned in the set position respective to the VAD 1101a. In some embodiments, the position of one or more VADs 1101a is easily recognized from outside the subject and/or the position of each of the one or more VADs 1101a is fixed with respect to an internal structure (e.g. a blood vessel 210). Using the VADs 1101a, measurements are optionally made at the same location and/or orientation on the internal structure at different times. For example, the measurement device 1159a may be moved between measurements and/or may be used to measure another location and/or another subject. The time between measurements of the same internal structure may range between a minute to 6 hours and/or between 6 hours and 3 days (for example between hemodialysis sessions) and/or between 3 days to a month and/or between a month to 6 months and/or between 6 months to 3 years. Repeating measurements of the same internal structure over time optionally facilitates detecting changes of the structure and/or its functioning (for example changes in the state of a blood vessel and/or blood flow). For example, an external ultrasound (US) probe may be used to measure changes blood velocity over time at a particular location. Measured changes may be processed for example to give an estimate of a degree of stenosis of the vessel. In some embodiments a gauge 1157a (for example with visible markings) may be used to position a sensor with respect to a VAD 1101a.

In some embodiments, for example as illustrated in FIG. 11B, two or more VADs 1101b, 1101c may be used as markers to position an external device 1159b. For example, multiple markers may facilitate more accurate aiming (e.g. positional translational and orientational rotational positioning than a single marker. For example, positioning may make use of a gauge 1157b. Alternatively or additionally, the external device 1159b and/or the VADs 1101b, 1101c may include position sensor that measures the relative position. The output of the position sensor may be processed and an indicator may signal to the operator when the sensor is in position and/or how to move it to reach the proper position. For example, the external device 1159b may include a position sensor with two light detectors that detect a location of one or more LED lights on the VADs 1101a, 1101b. Optionally an indicator (for example on the VAD 1101c, 1101b, on the external device 1159b and/or on a network device) instructs the operator how to move the external device 1159b in order to reach the correct position. When the position is reached, an OK indicator is activated and/or the device 1159b may automatically take a measurement. External device may include any of the hardware and/or software discussed in various embodiments described herein, for example in regards to FIGS. 3D and/or 3E. For example, external device may include a sensor (e.g. an US flow meter) and/or processor, and/or a communication device (e.g. a transceiver), a power source, an indicator/screen, a body attachment device, a memory for velocity readings, reports generator and/or encryption circuit for example to protect privacy and security. The VAD may include aspects as described herein above and/or below and/or any combination of details of various embodiments described herein.

Figure 12:
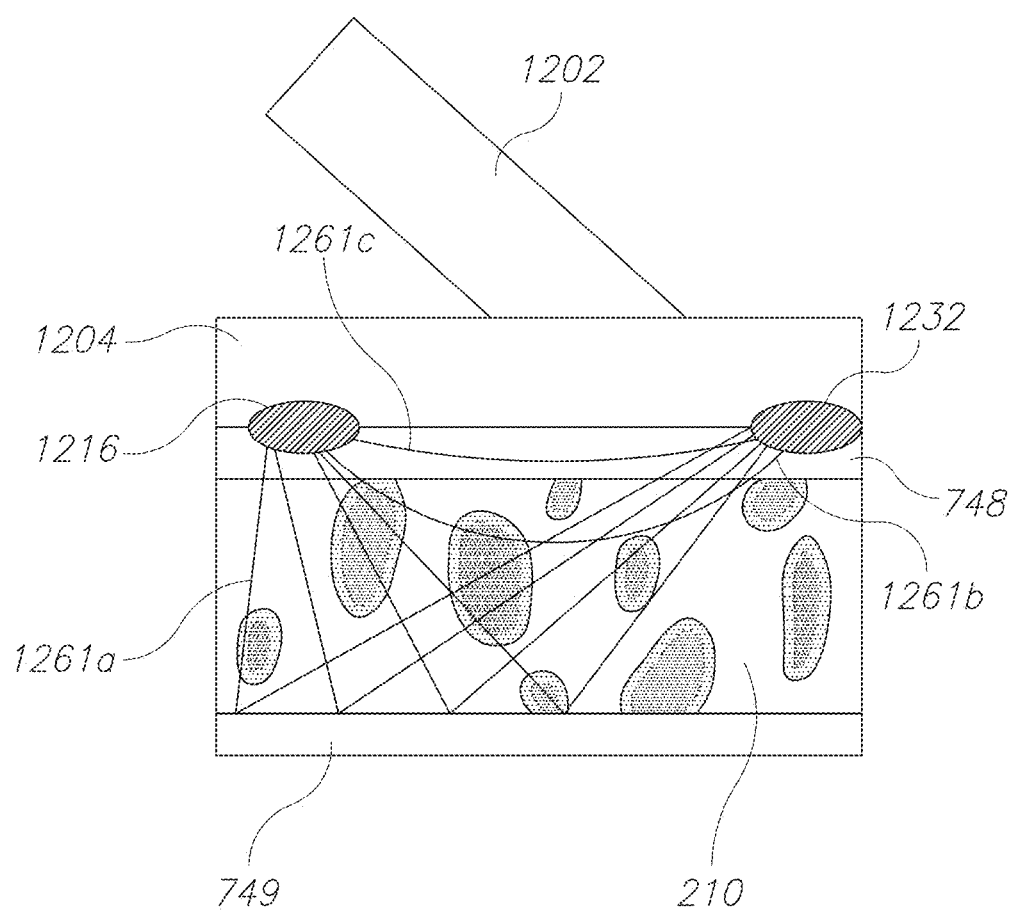
FIG. 12 is a schematic illustration of measuring characteristics of a blood vessel in accordance with an embodiment of the current invention.

FIG. 12 is a schematic illustration of measuring characteristics of a blood vessel in accordance with an embodiment of the current invention. In some embodiments an actuator 1216 may send a signal 1261a, 1261b and/or 1261c. Optionally the signal 1261a, 1261b and/or 1261c is measured by a sensor 1232. For example, the sensor may be located at a fixed location different to from the actuator 1216. For example, from the change of the timing and/or strength of the signal between the actuator 1216 and the sensor 1232, a characteristic of the structure may be measured.

In some embodiments, actuator 1216 may include an emitter of an electromagnetic beam (for example a light emitter e.g. a near infrared emitter) at a determined frequency. Optionally part 1261c of the signal propagates through the vessel from wall 748 to a sensor 1232 and/or part 1261b of the signal propagates through the lumen of vessel 210 (e.g. through the blood) to sensor 1232 and/or part 1261a of the signal reflects off a back wall 749 to sensor 1232. Optionally, analysis of the timing of the signal and/or the mix of frequencies and/or distortion of the beam (e.g. frequency and/or phase) at sensor 1232 optionally is correlated with a characteristic of the vessel. For example, the measured signal may be used to estimate a condition of the vessel (for example the thickness of a wall of the vessel). Alternatively an upstream actuator may transmit a measurable signal to the blood (for example a magnetic signal and/or a change in temperature etc.) a downstream sensor will sense the signal. The time lag between transmitting the signal and sensing the signal may be used to estimate blood velocity.

In some embodiments, a VAD may include a vessel interface 1204 (e.g. a footplate) and/or a guide 1202 (e.g. a cylindrical guide). Optionally, actuator 1216 and/or sensor 1232 are located on the vessel interface 1204. Alternatively or additionally, an actuator may be located on one VAD and/or a sensor on another VAD. Alternatively or additionally, one or more components may be separate from the VAD.

Figure 13A:
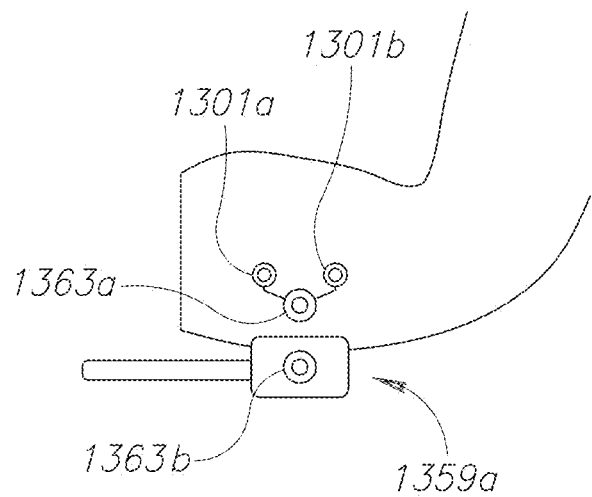
FIGS. 13A and 13B are schematic illustrations of charging a device in accordance with embodiments of the current invention.

FIG. 13A is a schematic illustration of charging devices in accordance with an embodiment of the current invention. In some embodiments, a charging device 1359a may be used to recharge a battery of an implant between uses. The charging device 1359a may comprise a wireless charger 1363b for wireless charging of a receiver 1363a implanted into the subject and/or connected to the VADs. For example, the wireless charger 1363b may include a coil for magnetic charging and/or a US device for ultrasonic charging or other charging methods. Optionally the charging device may be positioned with respect to one or more VADs 1301a, 1301b and/or with respect to an implanted control box.

Figure 13B:
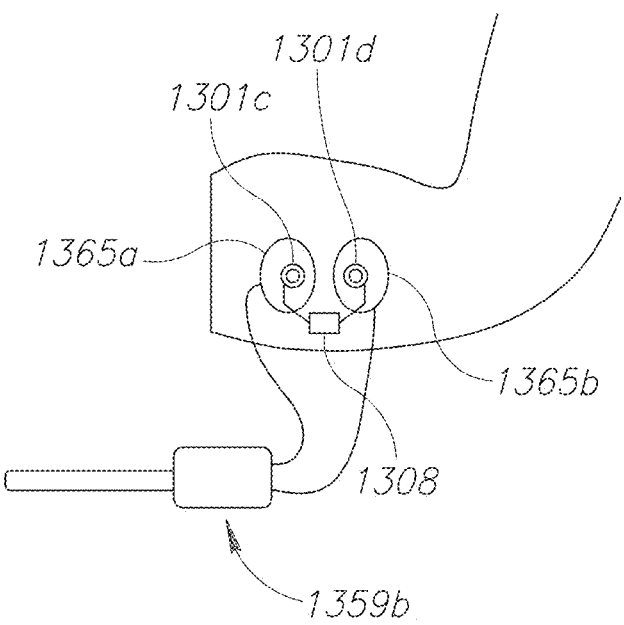

In some embodiments, for example as illustrated in FIG. 13B, a charging device 1359b may take advantage of two conductive conduits (e.g. guides of VADs 1301c and 1301d) are implanted just under the skin, with both conduits connected to the same electronic circuit implant 1308 (for example including a power source).

The user can induce sufficient current through the implant to change its internal batteries by applying a DC and/or an AC voltage source connected to two electrodes 1365a and 1365b attached on the skin over and/or close to the two conduits. The voltage of the source is optionally low enough not to be felt by the patient (e.g. in the 0.1-10V range), and/or high enough to deliver enough current to charge the implant. It may be preferable to design the implant charging circuit to operate at a low input voltage, for example to minimize leakage current between the conduits which may flow through the tissue parallel to the current through the implant. Using high frequency source in the 1 KHz to 100 MHz range optionally decreases the electrode to skin impedance, so higher currents may be used at lower voltages. High frequency optionally also decreases the patient's discomfort.

Figure 14:
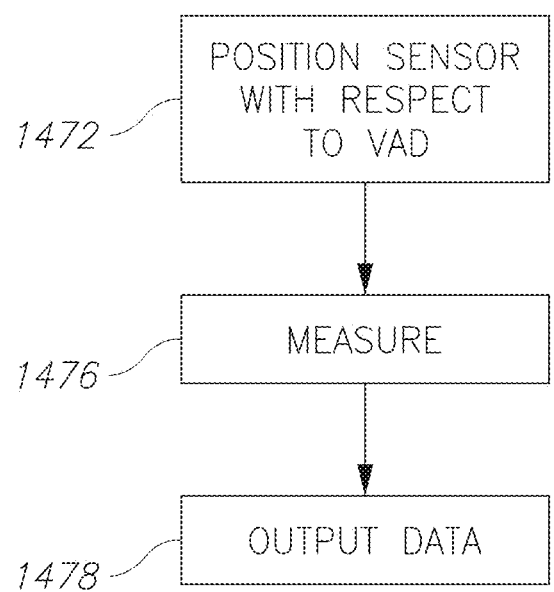
FIG. 14 is a flowchart illustration of measuring a physiological parameter in accordance with an embodiment of the current invention.

FIG. 14 is a flowchart illustration of measuring a physiological parameter in accordance with an embodiment of the current invention. In some embodiments, hemodynamics of a vessel (for example an AV fistula) will be characterized based on measured blood velocity. For example, a measuring device may use a U/S Doppler technology. Optionally measurement 1476 is enhanced by accurate placement 1472 of the measuring device via markers. For example, a marker may be embedded in a VAD implant. The measurement optionally provides early indication that may help decide whether the patient should be referred to higher level testing.

In some embodiments, measured blood velocity is used to indicate effect of a narrowing of a vessel's cross-section. Velocity which is linked inversely to the cross-section changes immediately when the cross-section changes and therefore, alert on deterioration when it begins. Alternatively or additionally, measurements may include blood flow volumetric flow. For example, volumetric flow may be measured with Duplex ultrasound. In some embodiments, flow velocity is more sensitive to cross sectional changes in the vessel and/or requires less expensive equipment then measuring volumetric flow.

In some embodiments, measurements of data from measurements may be stored on the external measurement device. Optionally, the device stores data from multiple patients and/or multiple measurements sessions. Optionally, the data enable early detection as well as trend analysis. The data and/or results of data processing may be output 1478 in a local user interface and/or to a clinician for according to privacy rules. Output 1478 may be routine after a measurement and/or periodically and/or in response to what was detected. For example, data and/or a warning may be output 1478 when data processing indicates that there may be a condition that may require intervention. Optionally, the data and/or processed statistics may allow early identification of AVF deterioration. Early identification and/or treatment may further help in preventing AVF deterioration. In case of an alert, the clinician will optionally be advised to send the patient to higher level diagnosis either by an ordinary U/S machine or by any other method.

In some embodiments, the above system may facilitate routine measurements (for example of blood velocity, wall thickness, stenosis). For example, measurements may be available whenever required. Alternatively measurement may be made before or after a dialysis session or at specific time-intervals or only when there's concern about the AVF status. In some embodiments, the system and method of measurement described herein may facilitate making measurements by the ordinary staff and without a need for specialized staff. Optionally, the system will automatically take care of positioning the U/S sensor and/or interpreting the results. For example, measurements may be taken by the staff of a dialysis clinic without requiring a certified U/S technician. For example, a blood velocity measurement is estimated to take between 0 to 3 minutes and/or between 3 to 10 minutes of nurse time.

In some embodiments, the accuracy of velocity measurement depends on accurate positioning of the measurement device vs. the blood vessel. For example, flow speed may be highly local. Optionally, the above methodology and/or system facilitates repeated measurements at the same location and/or facilitates using flow velocity for analysis of stenosis. For example, this may be achieved by using the locations of the VADs to align the measurement device precisely and repeatedly at every measurement, preferably as in-line as possible with the AVF axis. Once set, optionally by a certified operator, the location coordinates are set on a ruler that is a part of the external measurement device. The non-certified operator will be instructed to place the Controller on the hand according to the rulers setting.

Some possible for locating the measurement device includes:

1. The measurement device may be connected to a transparent ruler that has a coordinate matrix marked on it. The preferred coordinates of the VAD are optionally noted (for example with respect to the entrance point) the first time the measurement is taken. At future readings, the nurse first adjusts the location of the ruler over the VADs' exit points to the same coordinates, and then takes the reading.

2. Same as above but a marker (such as LED lights) on a proximal end of at least one of the VADs replaces the marker on the exit points as a reference locator. This may increase positional accuracy but presents a concern if LEDs visibility will be sufficient with challenging skin colors and ambient lighting conditions.

3. The system incorporates at least one detector that detects the alignment between the VADs and the external device. For example, a detector in the external measuring device may detect a LED light from the VAD and instruct the operator how to move the ruler to reach the correct, location. When the exact location is reached, the Controller shows a green light and/or automatically begins measurement. For example, this automatic procedure may reduce the required operator expertise.

In some embodiments, flow may be measured using a fixed sensor. For example, sensors may be placed around the blood vessel. For example, a change in voltage between electrodes that is caused by flow of electrically-charged blood cells may be measured. For example, an actuator may be placed upstream including an electrically powered coil. Optionally the coil may surround most and/or all of the blood vessel in a cross section. The coil may apply magnetic field that is influenced by the electrically-charged blood cells. A change in the flow generates a change in the electrical field that exerts voltage gap between the electrodes that generate this field. The voltage gradient is optionally sensed. For example, the vascular access device may include a component that is placed around the vessel. Optionally that component may be used for the actuator and/or sensor. Optionally, a portion of a device surrounding a blood vessel may be larger than the vessel (for example when the device is installed to an immature fistula). Optionally this will enable increase in the vessel diameter as it matures.

In same embodiments, blood velocity measurements may be taken by implanted sensors at a distal portion of a vascular access device (and/or on two vascular access devices of for example between 0 to 4 cm and/or 3 to 7 cm and/or 7 to 20 cm apart). For example, a sensor may use bi-directional Doppler technology to assess blood velocity within the vessel. Readings are optionally sent to an external reader for example using a wireless transmitter.

In some embodiments, a vibration sensor for example a microphone is used to detect and/or quantify turbulence intensity within the vessel. For example, the sensor may be attached to the implant adjacent to vessel's wall. In some embodiments, the artery-vein anastomoses angle, vein curvature and placement during the surgery affect blood flow and specifically turbulence within an AV Fistula. Optionally turbulence measurements may be made within the vessel before a surgeon closes the incision. The surgeon optionally may adjust to vessel to improve the turbulence and/or flow. This tool may reduce the failure rate of fistulae.

In some embodiments, a Glucose sensor may optionally be attached to an implant (for example a VAD).

Figure 15:
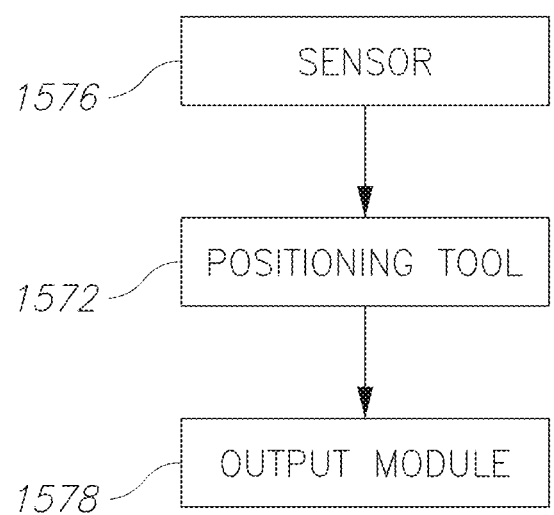
FIG. 15 is a block diagram of a measurement system in accordance with an embodiment of the current invention.

FIG. 15 is a block diagram of a measurement system in accordance with an embodiment of the current invention. For example, a measurement system may measure anatomical and/or physiological characteristics of a subject. In some embodiments a measurement system may include a sensor 1576. For example, a sensor 1576 may include a U/S sensor and/or a light sensor. Optionally, the system includes a positioning tool 1572. For example, the positioning tool 1572 is used to position the sensor with respect to one or more VAD. The positioning tool 1572 may include mounting the sensor permanently on the VAD. Alternatively or additionally, the positioning tool 1572 may include a physical measuring and/or positioning device (for example a positioning template). Alternatively or additionally the positioning tool 1572 may include a positioning application for example sensor and indicator that indicates to a user when the sensor is properly positioned. Alternatively or additionally the positioning system may include an automatic positioner and/or activator that activates the sensor when it is in the right position. In some embodiments, a measurement system includes an output module 1578. The output may include a computer readable memory and/or a wireless transmitter and/or a network communication device and/or a user interface (for example including a microphone and/or a speaker and/or a view screen and/or a touch screen.

In some embodiments, sensor system may include an actuator, for example to send a signal that will interact with a subject's body and be measured to measure physiological and/or anatomical characteristics of a subject.

Figure 16A:
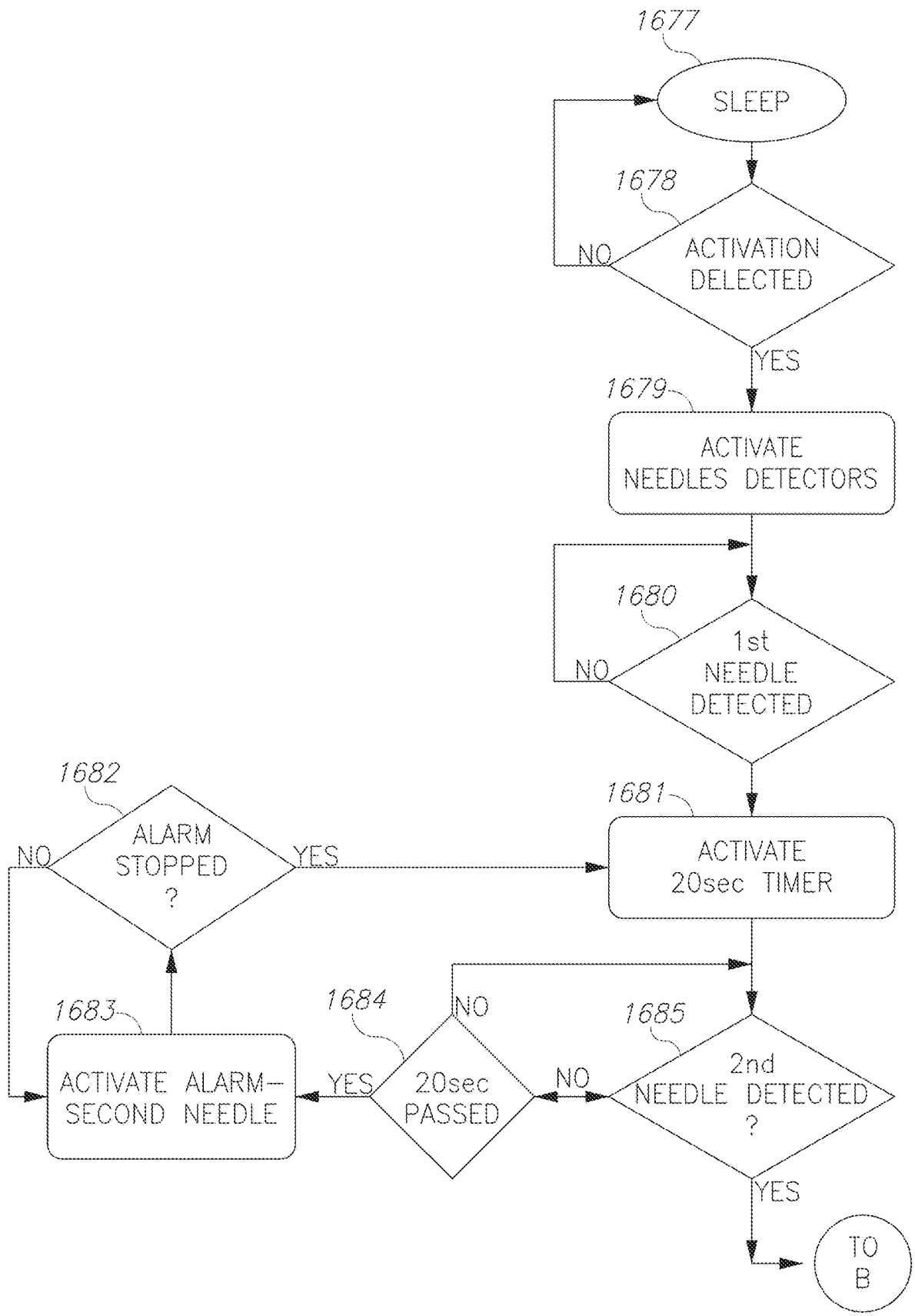
FIGS. 16A-16C are a flow chart illustration of accessing a blood vessel in accordance with an embodiment of the current invention.
Figure 16B:
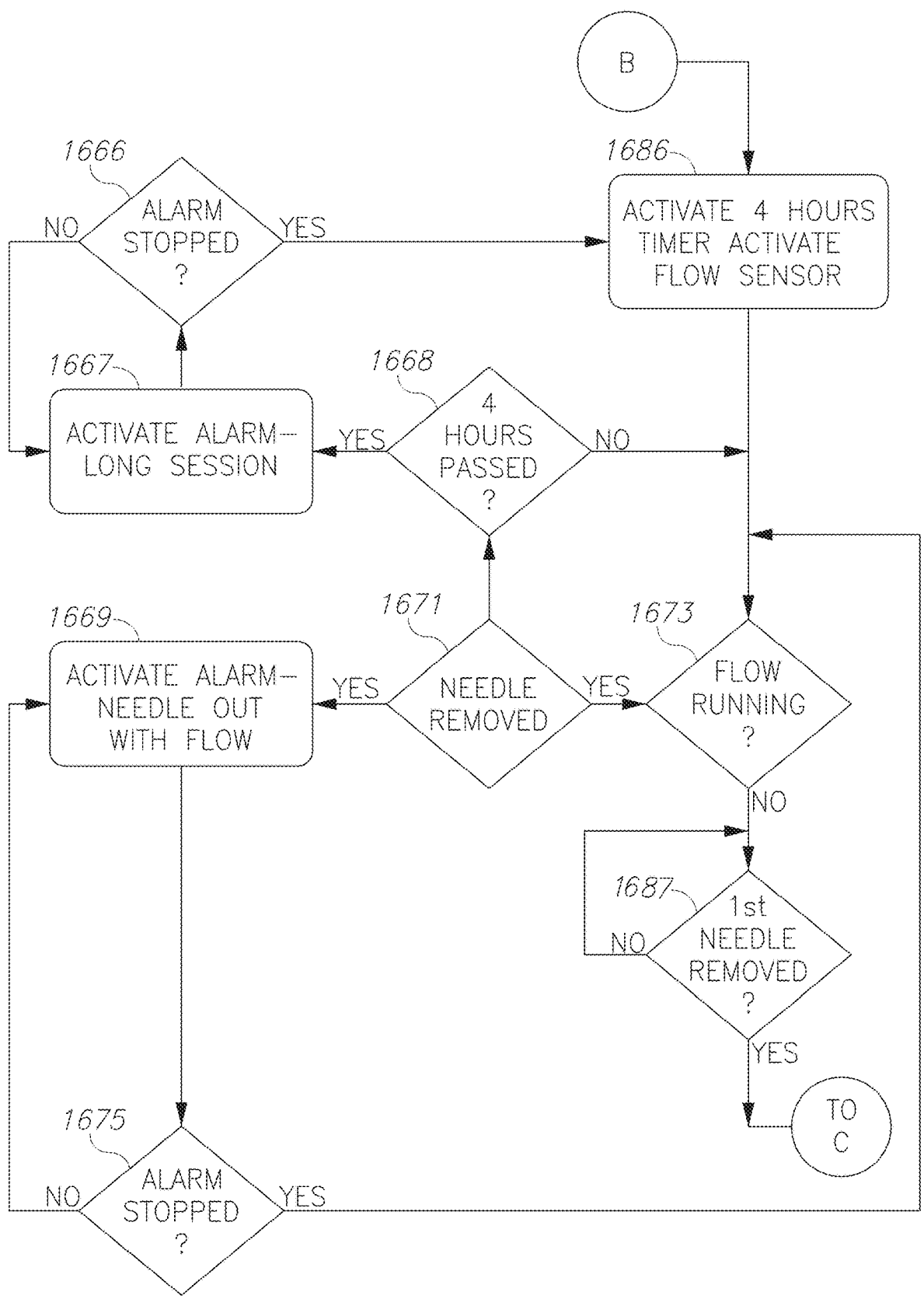
Figure 16C:
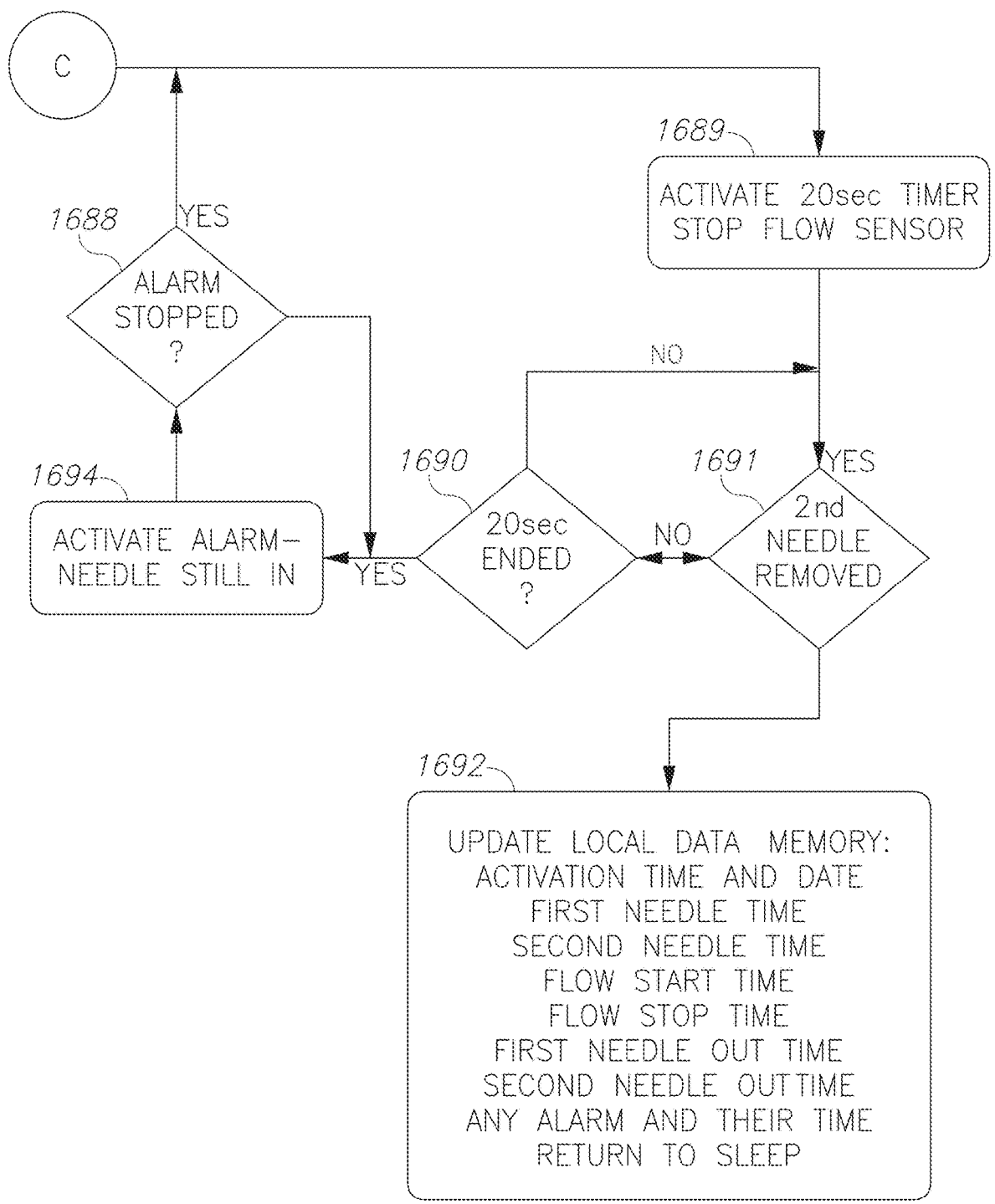

FIGS. 16A-16C are a flow chart illustration of activating and/or using a system of VADs for hemodialysis in accordance with an embodiment of the current invention. Optionally the system includes two VAD devices and/or an implanted controller circuit. In some embodiments, when not in use, active devices on the VAD system are in a sleep state 1677. Optionally the system is activated 1678. For example, activation 1678 may occur due to an external stimulation. For example, activation may be by applying stimulation (for example via a flashing light source and/or a magnetic key and/or tapping) to one or either of the VADs and/or to the skin in the vicinity of the VADs and/or to a location of the implanted controller. Optionally the flashing light source and/or magnetic key is incorporated into an external device (for example, a sensor device and/or a controller).

In some embodiments, once an activation signal is detected, a needle sensor is optionally activated. 1679. Alternatively a ready indicator is triggered. Optionally the needle sensor repeatedly checks 1680 for the presence of a needle tip in a critical zone. In some embodiments, the system will continually enforce an order (e.g. that a needle should be inserted in a first VAD before a second VAD). Optionally, if a needle is inserted in the wrong order (e.g. into the second VAD before the first VAD) then the device may issue a warning. Optionally, the ready indicator (for example a green LED) will also indicate the proper VAD for insertion. For example, when the system is activated, the light may be lit near the location of the first VAD. After the first needle has been detected 1680, the light may be lit near the second VAD.

In some embodiments, after insertion of a first needle is detected 1680 in a VAD, the system waits 1681 a predetermined period of time for example 20 seconds for insertion of a second needle (e.g. into a second VAD). When the time passes 1684 without a second needle being inserted, the system optionally triggers an alarm 1683. Optionally the system includes a way for a practitioner to stop 1682 the alarm. When the alarm is stopped 1682 the waiting period is optionally restarted. In some embodiments, the length of the waiting period between needles may range for example between 10 to 40 seconds and/or between 1 to 10 seconds and/or between 30 sec. to 2 minutes and between 2 to 10 minutes and/or between 10 minutes to 30 minutes. Optionally, during the waiting, in a VAD into which a needle has not yet been inserted a detector repeatedly checks 1685 for insertion of a needle.

In some embodiments, during the waiting period, in a VAD in which a needle has been inserted, the sensor repeatedly checks if the needle is removed. For example, when a needle is removed, the system may give a warning. After all the needles are removed system may give an acknowledgement and/or shut down. Optionally, shut after may occur after a waiting period of for example 25 seconds. In some embodiments, the length of the waiting period after removal of all needles before shut down may range for example between 10 to 40 seconds and/or between 1 to 10 seconds and/or between 30 sec. to 2 minutes and between 2 to 10 minutes and/or between 10 minutes to 30 minutes.

The system may continue to monitor needle insertion until needles are inserted into two or more VADs. Once the requisite number of needles has been inserted, the system may activate 1686 a treatment timer (for example for four hours 1668). Alternatively or additionally the treatment time may last for a time ranging between 30 minutes to 3 hours and/or between 3 hours to 5 hours and/or between 5 hours and 10 hours. While the treatment timer is running, the system may repeatedly check that blood is flowing 1673 through the system and/or that all of the needles remain in place. If the time has expired 1668 and treatment hasn't finished a long session warning may be issued 1667. Stopping 1666 the alarm may optionally starts a new timer 1686.

In some embodiments, one needle remaining in place after another needle has been removed 1671 and/or while flow is running 1673 could indicate that a needle has become dislodged during treatment, a potentially a life-threatening situation. In some embodiments when it is detected that a needle has been removed 1671 while flow is running 1673 and/or a second needle is in place, an alarm is immediately triggered 1669. For example, a very obvious alert message is send to the relevant clinical staff. In some embodiments, there may be a waiting period after removal 1671 of a portion of the needles before the alarm is triggered 1669. For example, the waiting period may range for example between 0 to 5 seconds and/or between 5 to 20 seconds and/or between 20 to 40 seconds and/or between 40 seconds to 1.5 minutes. Stopping 1675 the alarm may optionally starts a new timer and/or an alarm until all the needles are removed and/or replaced.

In some embodiments, removal 1687 of a portion of the needles (e.g. one of two needles) after flow has stopped 1673 activates 1689 a timer (for example 20 seconds). When the rest of the needles (e.g. second needle) is removed then system may perform 1692 a shutdown routine When the time period ends 1690 while a portion of the needles are still in 1691 the subject, an alarm may be triggered 1694. Optionally the system includes a way for a practitioner to stop 1688 the alarm. When the alarm is stopped 1688 the waiting period is optionally restarted. In some embodiments, the length of the waiting period between needles may range for example between 10 to 40 seconds and/or between 1 to 10 seconds and/or between 30 sec. to 2 minutes and between 2 to 10 minutes and/or between 10 minutes to 30 minutes. Optionally, during the waiting, in a VAD into which a needle has not yet been removed a detector repeatedly checks for insertion of a needle and/or in a VAD from which the needle has been removed, the system repeatedly checks for reinsertion of the needle. Optionally the shutdown routine may include some or all of the following actions: update a local memory, record a time and date of the following insertion of the first needle, insertion of the second needle, start flow, stop flow, remove first needle, remove second needle, triggering of alarm, and return to sleep mode.

In some cases, a VAD may be activated for reading data and/or measuring and/or reprogramming without actually performing a dialysis treatment.

Figure 17:
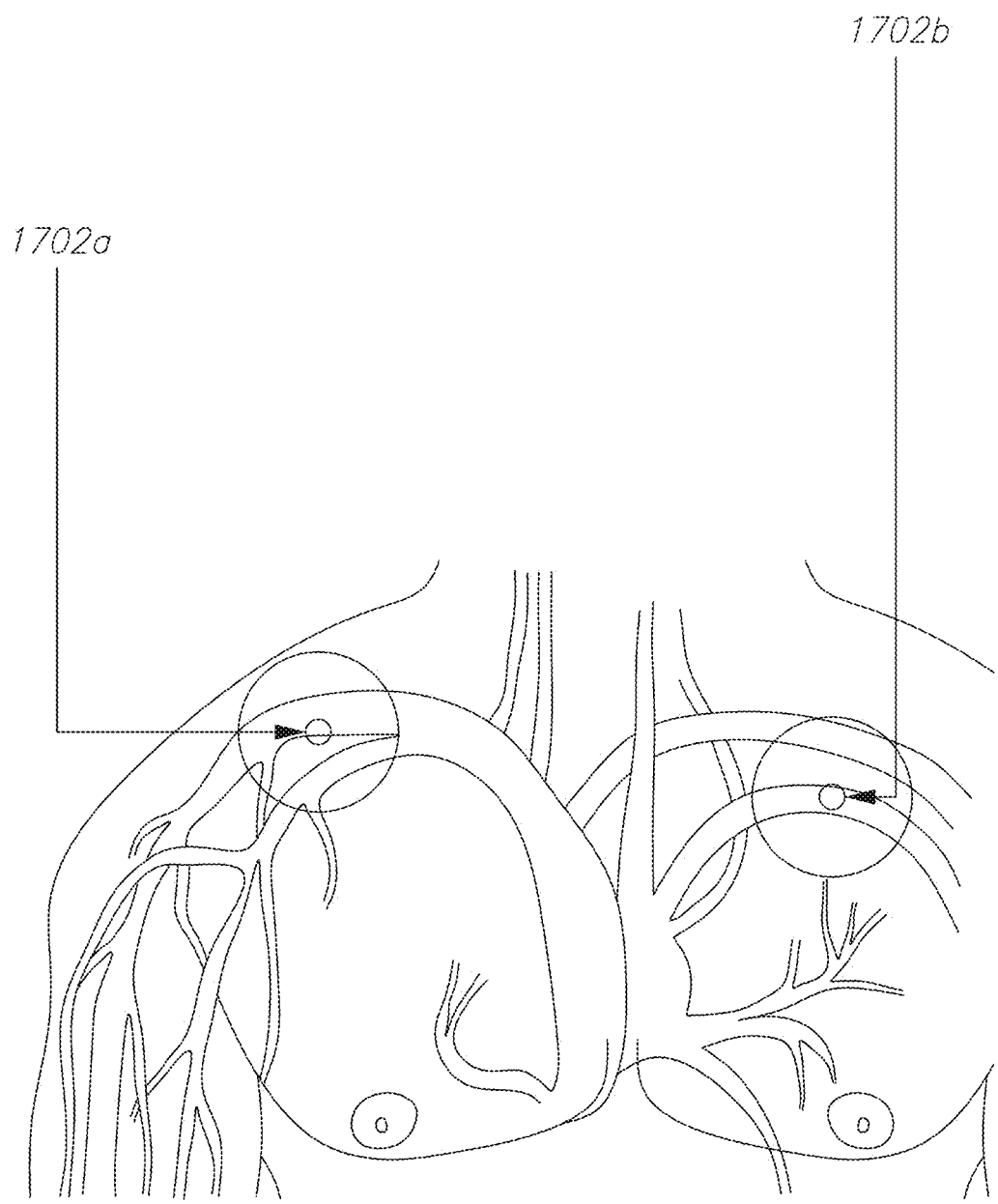
FIG. 17 illustrates some further uses of VADs in accordance with an embodiment of the current invention.

FIG. 17 illustrates some further uses of VADs in accordance with an embodiment of the current invention. In some embodiments, one or more VAD's (for example as described in any of the embodiments described herein above) will be connected directly to a natural blood vessel. For example, one or more VADs 1702*a* may be connected to a high flow vein and/or a vein that is on or near the central venous system (for example an auxiliary vein in the chest wall that is within several cm of the central venous system or the basilic vein that is in the upper arm and has diameter and flow at internal venous pressure, 6-8 mmHg, that are similar to the fistula that is under arterial pressure—80-120 mmHg). Optionally a needle (for example including a plastic needle and/or catheter) would be directed along the guide of the VAD 1702*a* into the central venous system. For example, during each dialysis session two needles would be place through two VADs 1702*a* into the central venous system to accomplish dialysis. Optionally, after dialysis, the catheter would be removed. For example, removing the needle/catheter may avoid complications of a long indwelling central venous line (e.g. permanent indwelling may incite a reparative process inside the lumen of the vessel as a reaction to the presence of a foreign body that can lead to occlusion of the central vein, a life-threatening complication). In some embodiments, having repetitive access to a high flow vein would eliminate the need to create a high flow vascular channel (a fistula) in the patient's extremity. For example, this could radically change the way dialysis is done.

In some embodiments, a VAD (for example as described in any of the embodiments described herein above) may be used for procedures other than dialysis. For existence, a VAD may be used for blood vessel access where repeated access is needed and/or access is needed to a high flow blood vessel. For example, some possible uses would be for chemotherapy and/or for treatment of a blood disorder. For example, a VAD 1702b may be used to get access to a central venous system artery.

In some embodiments a VAD may be implanted using a minimally invasive procedure.

Figure 18:
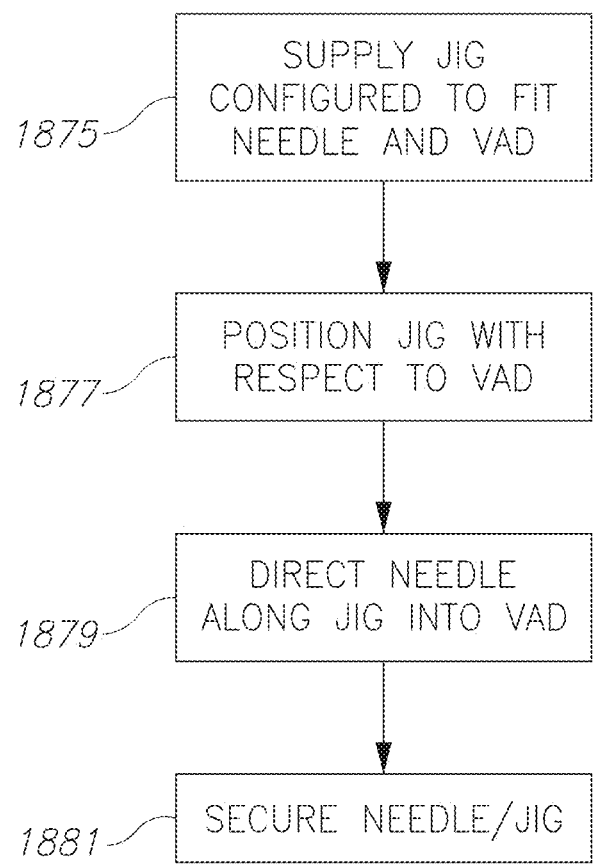
FIG. 18 is a flow chart illustrating a method employing an external jig while inserting a needle into a VAD in accordance with an embodiment of the current invention.

FIG. 18 is a flow chart illustrating a method employing an external jig in accordance with an embodiment of the current invention. For example, the jig may be employed while inserting a needle into a VAD. In some embodiments, a jig is sized to facilitate proper needle insertion into a JEM.

In some embodiments, the jig may be supplied 1875 to facilitate needle proper needle insertion. For example, the jig may be configured to facilitate needle insertion at a proper angle. Optionally, the jig may include needle channel and a base at an angle equal to an angle between a guide of a VAD and a skin interface.

In some embodiments, the jig may be supplied 1875 to facilitate needle insertion to the proper depth. For example, the jig may include needle channel having a length equal the difference between the length of a needle and the combined length of the VAD and desired insertion length into the vessel. For example, in a case where the VAD has a length of 16 mm and it is desired to insert 5 mm of a 25 mm needle into the vessel the needle channel of the jig may have a length of 4 mm. Optionally, in the case where a VAD has a custom length, the length of the jig may also be selected to facilitate proper needle insertion with a standard-length needle. For example, the length of a jig may be adjusted (for example by cutting to size).

In some embodiments, a jig may be positioned 1877 on the skin on a subject. For example, before inserting a needle the jig may be positioned 1877 with a needle outlet position at the beginning of the guide of the VAD. Optionally, the channel of the jig is oriented in the same direction as the guide of the VAD. For example, the VAD may include a direction indicator (for example a line of lights and/or lights that proceed in a particular direction like landing lights). Alternatively or additionally, before placing the jig an operator may determine the position of the VAD (for example by feeling the skin for the VAD position) and/or mark the skin showing the proper position and/or orientation. Optionally the channel of the jig is directed at an angle with the skin equal to the angle of the guide of the VAD with the skin. For example, when the angle between the base of the jig and the channel is the same as the angle between the skin interface of the VAD and the guide then the angle of the channel with the skin may be directed by placing the base of the jig flat against the skin. Optionally the jig may be held steady. For example, the base of the jig may include an adhesive and/or a non-slip surface to steady the jig on the skin. Alternatively or additionally, the jig may be held to the skin by a strap, tape and/or another means.

In some embodiments, a jig will direct 1879 a needle properly into a guide of a VAD. For example, the needle may slide along the channel of the jig to the guide. For example, the needle may be inserted after the jig has been properly positioned 1877.

In some embodiments, a jig may be used to secure 1881 a needle after insertion. For example, after needle insertion the needle and/or jig may be taped to the skin of the subject. Optionally securing 1881 a needle with a jig allows the needle to be secured during dialysis in the preferred angle of the VAD. For example, the needle is secured without flattening the needle against the skin and/or without deforming the blood vessel.

Figure 19:
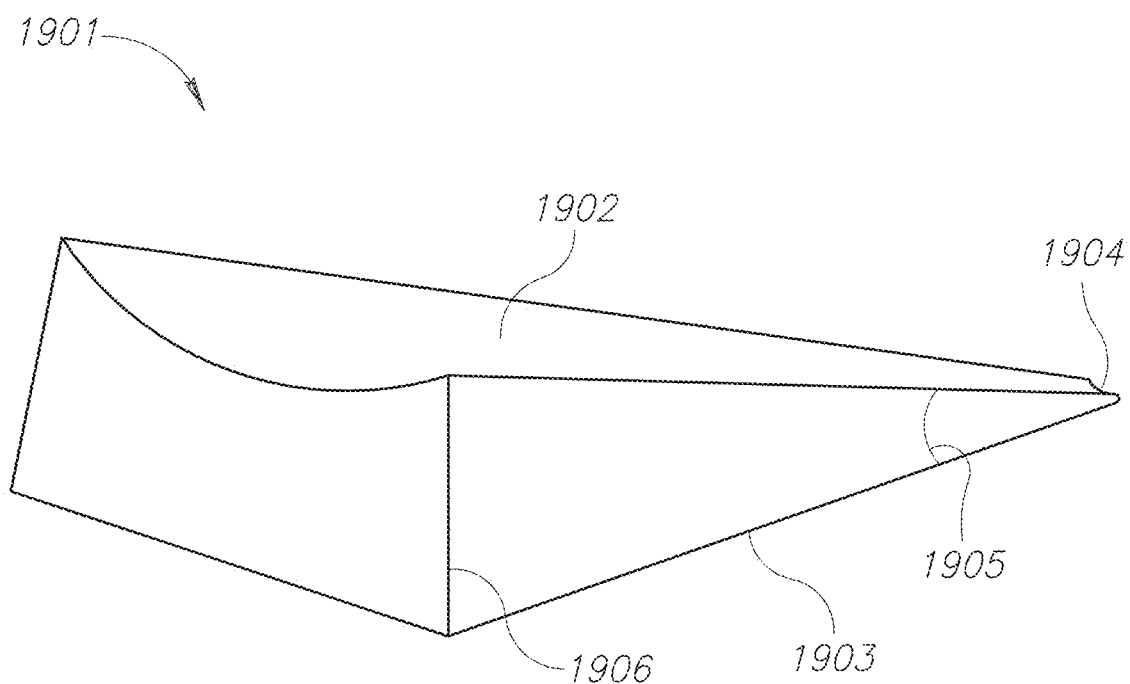
FIG. 19 is a schematic illustration of a jig in accordance with an embodiment of the current invention.

FIG. 19 is a schematic illustration of a jig 1901 in accordance with an embodiment of the current invention. In some embodiments jig 1901 includes a needle channel 1902. Optionally an angle 1905 of the needle channel with a base 1903 of the jig 1901 is configured to direct the needle at a preferred angle to the skin. Optionally, walls 1906 of the jig are angled outward. For example, the angling the walls 1906 outward may increase the surface area of the base 1903 with respect the channel 1902 and/or make the jig sit more stably on the skin. For example, the jig 1901 may have a prismatic shape with a channel 1902 fitting the needle. Optionally a needle outlet 1904 is located at an end of the channel closest to the base 1903.

In some embodiment a jig 1901 will be configured for single use. For example, the jig may be made of plastic and/or silicone. Alternatively or additionally, the jig may be configured for multi-use. Optionally, the jig may be designed for sterilization. For example, the jig may be made of stainless steel. A jig may be supplied with a VAD and/or may be supplied separately, for example in a one use sterile package.

Figure 20:
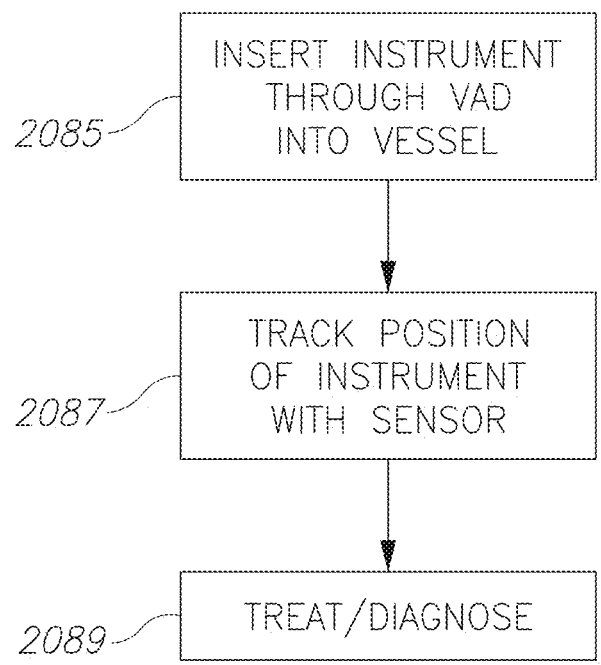
FIG. 20 is a flow chart illustration of method of inserting a device through a VAD in accordance with an embodiment of the current invention.

FIG. 20 is a flow chart illustration of method of inserting 2085 a device through a VAD in accordance with an embodiment of the current invention. In some embodiments, a VAD may be used to gain access to a vessel for a diagnostic and/or therapeutic device. For example, a catheter may be inserted 2085 through a VAD into a vessel. For example, a VAD may be used to access a vessel to perform angioplasty and/or a thrombectomy. Optionally, a stent may be inserted 2085 through a VAD into a vessel.

In some embodiments, a sensor may be used to track 2087 an instrument inserted through a VAD. For example, a needle sensor may be used to determine when a catheter has reached the vessel. Alternatively or additionally, a VAD may include an optical sensor for sensing needle insertion. Optionally an instrument inserted into the VAD will include optical markings that will be detected by the sensor and help determine the position and/or status of the instrument. Similar for other sensors (for example a magnetic sensor) the instrument may include other markings (for example metal strips). In some embodiments a VAD will be used to implant a device and/or to upgrade (e.g. hardware and/or software) of an existing implant.

In some embodiments, while an instrument is in the vessel it may be used to treat and/or diagnose 2089 the vessel. Alternatively or additionally, the vessel may be used to access other structures and/or the instrument may be used to treat and/or diagnose 2089 those structures. For example, a VAD in a central vein may be used to supply access to the heart and/or lungs.

Figure 21:
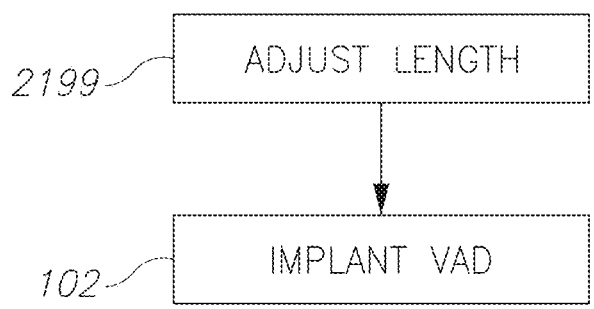
FIG. 21 is a flow chart illustrating installing an adjustable length VAD in accordance with an embodiment of the current invention.

FIG. 21 is a flow chart illustrating installing an adjustable length VAD in accordance with an embodiment of the current invention. In some embodiments, a length of a VAD may be adjusted 2199 before the VAD is implanted 102. For example, the VAD may telescope and/or be trimmed to size. Optionally adjusting the length of the VAD may make it possible to achieve a desired angle of needle insertion independent of the depth to the vessel.

It is expected that during the life of a patent maturing from this application many relevant technologies will be developed and the scope of the terms are intended to include all such new technologies a priori.

As used herein the term "about" refers to ±10%

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range. When two ranges are connected with an and/or connector then the ranges may be separate and/or continuous. For example if a parameter is said to range between 1 to 3 and/or between 3 to 5 and/or 5 to 7 then the ranges 1 to 5 and 5 to 10 and 1 to 10 are also included.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. An implantable device for vascular access, comprising:
    a guide including a lumen shaped and sized to fit a hemodialysis needle constraining the needle to an angle of less than 5 degrees with respect to the lumen and constraining a position of a distal tip of the needle to a target of less than 90 mm$^2$ at a distal end of said lumen on a front wall of a blood vessel;
    a sensor attached to said guide, said sensor configured to send a signal when a tip of said needle passes a predetermined position within 4 mm of and proximal of said distal end of said lumen; and
    an indicator responsive to said signal and to produce a signal visible to a practitioner through a skin of a subject.

2. The device of claim 1, wherein a length of the lumen is between 7 mm and 70 mm.

3. The device of claim 1, wherein a length of the lumen is between 7 mm and 35 mm.

4. The device of claim 1, wherein the lumen has an average inner width of between 2 mm and 7 mm.

5. The device of claim 1, wherein said indicator is mounted on said guide.

6. The device of claim 5, wherein said indicator is configured to be visible from outside through said skin under indoor fluorescent lighting.

7. The device of claim 1, further comprising a vessel interface configured for connecting said guide to the front wall of a blood vessel.

8. The device of claim 7, wherein said lumen is surrounded on at least three sides by said vessel interface.

9. The device of claim 1, further comprising: a skin interface configured for attaching said guide to said skin.

10. The device of claim 9, wherein a proximal end of said lumen is surrounded on at least three sides by said skin interface.

11. The device of claim 9, wherein a proximal end of said lumen passes through said skin interface.

12. The device of claim 1, wherein said sensor includes at least one of sensing a metal detector, a magnetic field detector, a light sensor, and a source.

13. The device of claim 1, further comprising an ultrasound emitter.

14. The device of claim 1, wherein said sensor measures a blood flow parameter.

15. The device of claim 1, further comprising a second sensor configured to measure attenuation of light by a wall of the blood vessel.

16. The device of claim 1, further comprising an implanted central control unit flexibly connected by an electrical conductor to the vascular access device.

17. The device of claim 1, wherein said sensor is an active sensor.

18. The device of claim 1, comprising an additional sensor is configured to measure a blood flow parameter of said blood vessel.

19. The device of claim 1, wherein the indicator is responsive to said signal from said sensor and is configured to produce an audible signal.

20. An implanted system, having a first vascular access device of claim 1, and further comprising:
a second vascular access device, comprising:
a second guide including a second lumen shaped and sized to fit a hemodialysis needle constraining the needle to an angle of less than 5 degrees with respect to the second lumen and constraining a position of a distal tip of the needle to a target of less than 90 mm$^2$ at a distal end of said second lumen on a front wall of a blood vessel,
wherein the second vascular access device is connected by an implanted metal conductor to the first vascular access device, said metal conductor providing electrical and/or data connection between said first vascular access device and said second vascular access device.

21. The system of claim 20, comprising:
a battery; and
a battery charging circuit conductively connected to said metal conductor for collecting energy from an electrical potential difference between said guide of said first device and said second vascular access device and charging said battery with said energy.

22. A method of vascular access comprising:
providing a guide including a lumen attached to a front wall of a blood vessel, configured for guiding a needle from a skin surface to a target at a distal end of said lumen on said front wall of said blood vessel;
inserting said needle along said guide from the skin surface to the target;
sensing when a tip of said needle passes a predetermined position in said guide proximal to a distal end of the guide and towards a lumen of said vessel;
indicating to a practitioner a result of said sensing; and
further inserting said needle along said guide at least 3 mm so that said needle extends out of said guide into said lumen of said vessel.

23. The method of claim 22, wherein said sensing is performed by a sensor mounted on said guide.

24. The method of claim 22, further comprising activating an alarm when said needle tip retracts outward from said predetermined position towards said skin surface during said passing blood.

25. The method of claim 24, further comprising:
passing blood through said needle between said blood vessel and a dialysis device.

26. The method of claim 24, further comprising:
providing a second guide attached to said front wall of said blood vessel, configured for guiding a second needle from said skin surface to a second target on said front wall of said blood vessel;
inserting said second needle along said guide from the skin surface to the target
wherein said activating said alarm occurs when one of said first needle or said second needle remains in said blood vessel while one of said first needle or said second needle retracts outward.

27. The method of claim 26, further comprising a method of charging an implanted device comprising:
providing a flexible electrical conductor connecting said guide to said second guide;
applying a voltage potential across said guide and said second guide;
passing a current along said electrical conductor between said guide and said second guide; and
storing energy from said current in an implanted device.

28. The method of claim 22, wherein said predetermined position is within 4 mm of the front wall of said blood vessel.

29. The method of claim 22, wherein said sensing includes at least one of sensing a metal object, sensing a magnetic field, sensing light reflected from said needle, and sensing a reduction of light blocked by said needle.

30. The method of claim 22, further comprising sensing attenuation of light by a wall of the blood vessel.

31. The method of claim 22, further wherein said guide includes a plug of tissue, the method further comprising: inserting said tip of said needle through said plug.

32. The method of claim 31, wherein said tissue includes vascularized tissue.

33. The method of claim 22, further comprising:
storing data on how long said needle tip was located inward of said predetermined position.

34. The method of claim 22, further determining a status of a blood vessel wherein said guide is permanently attached to a fixed location on the blood vessel, the method further comprising:
aiming a sensor relative to the vascular access device; and
measuring a parameter of the blood vessel at a predetermined location on the blood vessel with said sensor.

* * * * *